US012747215B2

(12) United States Patent
Gerard et al.

(10) Patent No.: US 12,747,215 B2

(45) Date of Patent: Sep. 29, 2026

(54) N2-ARYLMETHYL-4-HALOALKYL-PYRIDAZIN-3-ONE CFTR MODULATORS FOR THE TREATMENT OF CYSTIC FIBROSIS

(71) Applicants: UNIVERSITE DE REIMS CHAMPAGNE-ARDENNE, Reims (FR); INSERM (INSTITUT NATIONAL DE LA SANTÉ ET DE LA RECHERCHE MÉDICALE), Paris (FR); UNIVERSITE DE ROUEN-NORMANDIE, Mont-Saint-Aignan (FR); CENTRE NATIONAL DE LA RECHERCHE SCIENTIFIQUE (C.N.R.S.), Paris (FR); INSTITUT NATIONAL DES SCIENCES APPLIQUEES DE ROUEN (INSA), Saint Etienne du Rouvray (FR); ECOLE NORMALE SUPERIEURE DE LYON, Lyons (FR); UNIVERSITE CLAUDE BERNARD LYON 1, Villeurbanne (FR)

(72) Inventors: Stéphane Gerard, Fismes (FR); Jean-Philippe Bouillon, Fresquiennes (FR); Abderrazzaq Bentaher, Saint Genis Laval (FR); Eric Henon, Reims (FR); Jacky Jacquot, Reims (FR); Janos Sapi, Reims (FR); Frédéric Velard, Heutregiville (FR)

(73) Assignees: Universite de Reims Champagne-Adrenne Reims (FR), Reims (FR); Inserm (Institut National de la Sante et de la Recherche Medicale, Paris (FR); Universite de Rouen-Normandie, Mont-Saint-Aignan (FR); Centre National de la Recherche Scientifique (C.N.R.S.), Paris (FR)

( * ) Notice: Subject to any disclaimer, the term of this patent is extended or adjusted under 35 U.S.C. 154(b) by 846 days.

(21) Appl. No.: 17/780,148

(22) PCT Filed: Nov. 30, 2020

(86) PCT No.: PCT/FR2020/052228

§ 371 (c)(1),
(2) Date: May 26, 2022

(87) PCT Pub. No.: WO2021/105641

PCT Pub. Date: Jun. 3, 2021

(65) Prior Publication Data

US 2023/0013304 A1 Jan. 19, 2023

(30) Foreign Application Priority Data

Nov. 28, 2019 (FR) ..................................... 19 13404

(51) Int. Cl.
*C07D 237/14* (2006.01)
*A61K 31/501* (2006.01)
(Continued)

(52) U.S. Cl.
CPC .......... *C07D 237/14* (2013.01); *A61K 31/501* (2013.01); *A61K 45/06* (2013.01); *C07D 401/04* (2013.01); *C07D 409/06* (2013.01)

(58) Field of Classification Search
CPC .. C07D 237/14; C07D 401/04; C07D 409/06; A61K 31/501; A61K 45/06; A61K 2300/00; A61P 11/00; A61P 11/06
See application file for complete search history.

(56) References Cited

U.S. PATENT DOCUMENTS

| | | | |
|---|---|---|---|
| 2008/0269206 A1 | 10/2008 | Russell et al. | |
| 2017/0247335 A1 | 8/2017 | Gerard et al. | |
| 2019/0248765 A1 * | 8/2019 | Parks ................... | C07D 403/06 |

FOREIGN PATENT DOCUMENTS

| | | |
|---|---|---|
| EP | 1156039 A1 | 11/2001 |
| EP | 1604984 A1 | 12/2005 |
| WO | 2018081381 A1 | 5/2018 |

OTHER PUBLICATIONS

The English translation of the International Search Report, mailed on Mar. 4, 2021, in the corresponding PCT Appl. No. PCT/FR2020/052228.

(Continued)

*Primary Examiner* — Jeffrey S Lundgren
*Assistant Examiner* — Alexander K. Showalter

(57) ABSTRACT

The invention relates to compounds of Formula I:

(I)

(Continued)

or pharmaceutically acceptable solvates thereof, as well as their use in the treatment and/or prevention of diseases or conditions associated with a dysfunction of CFTR channel activity, in particular cystic fibrosis.

9 Claims, 3 Drawing Sheets

(51) Int. Cl.

| | |
|---|---|
| ***A61K 45/06*** | (2006.01) |
| ***A61P 11/00*** | (2006.01) |
| ***A61P 11/06*** | (2006.01) |
| ***C07D 401/04*** | (2006.01) |
| ***C07D 409/06*** | (2006.01) |

(56) References Cited

OTHER PUBLICATIONS

The English translation of the Chinese Office Action, mailed on Jul. 29, 2023, in the related Chinese Appl. No. 2020800924018.

* cited by examiner

[Fig. 1]
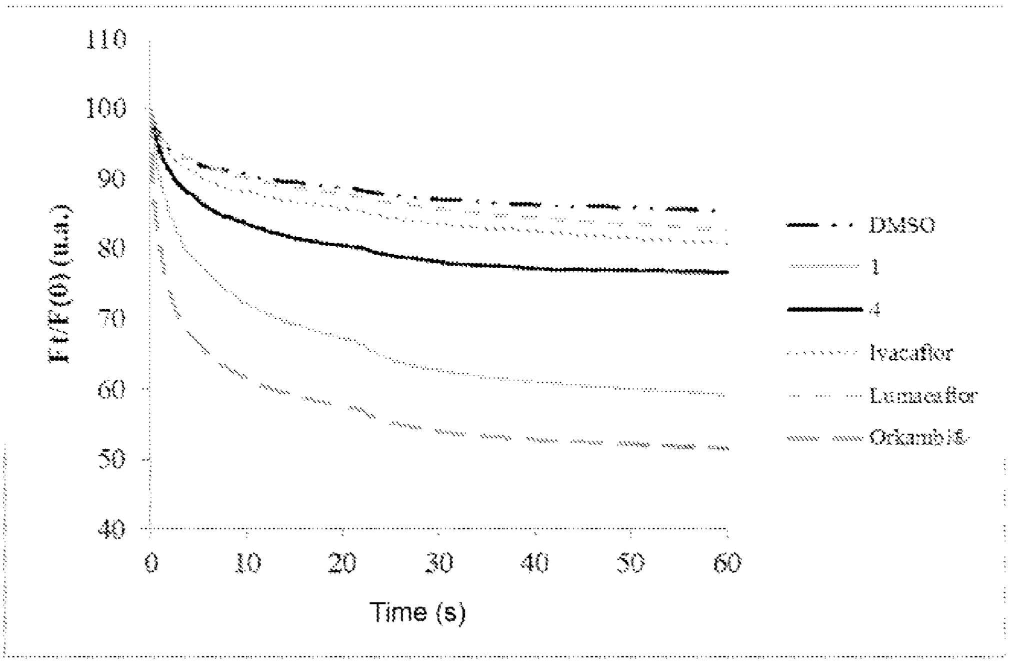
[Fig. 2]
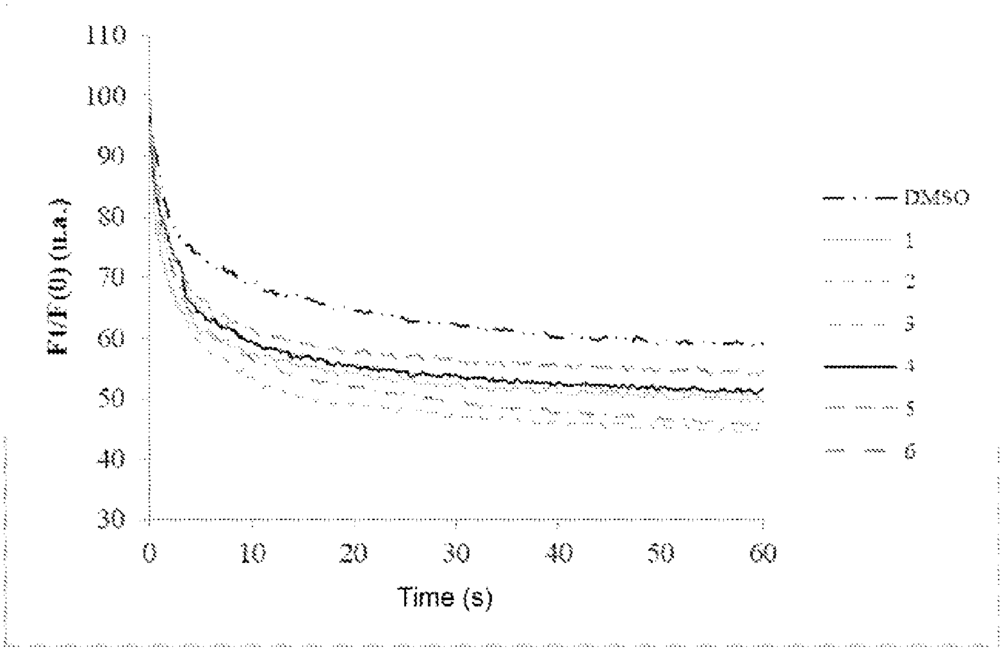

[Fig. 3]
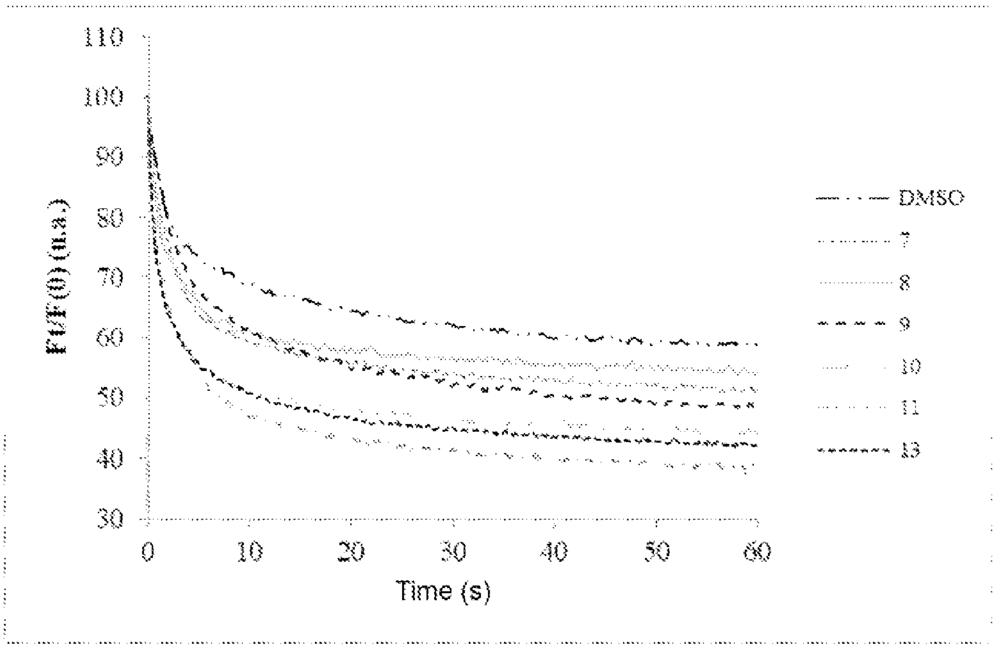
[Fig. 4]
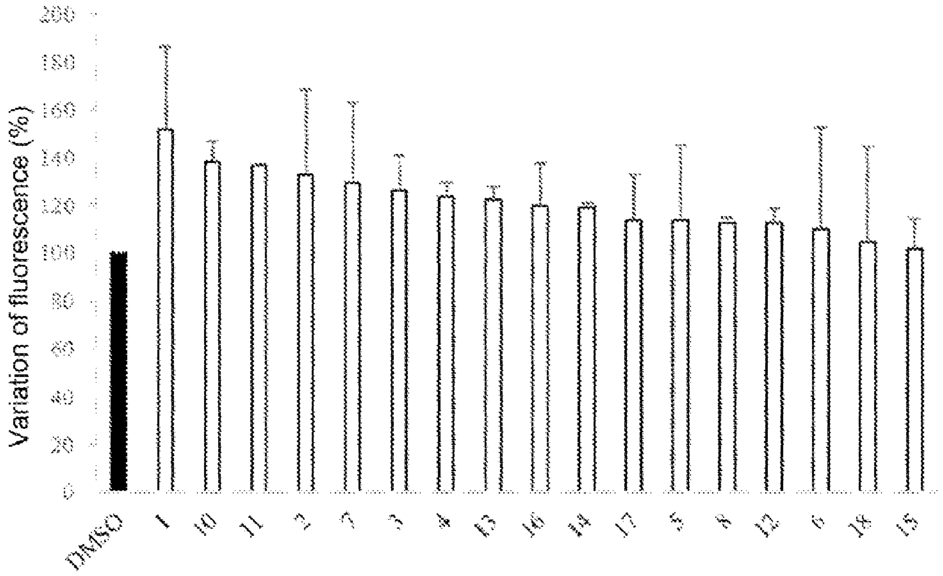

[Fig. 5]
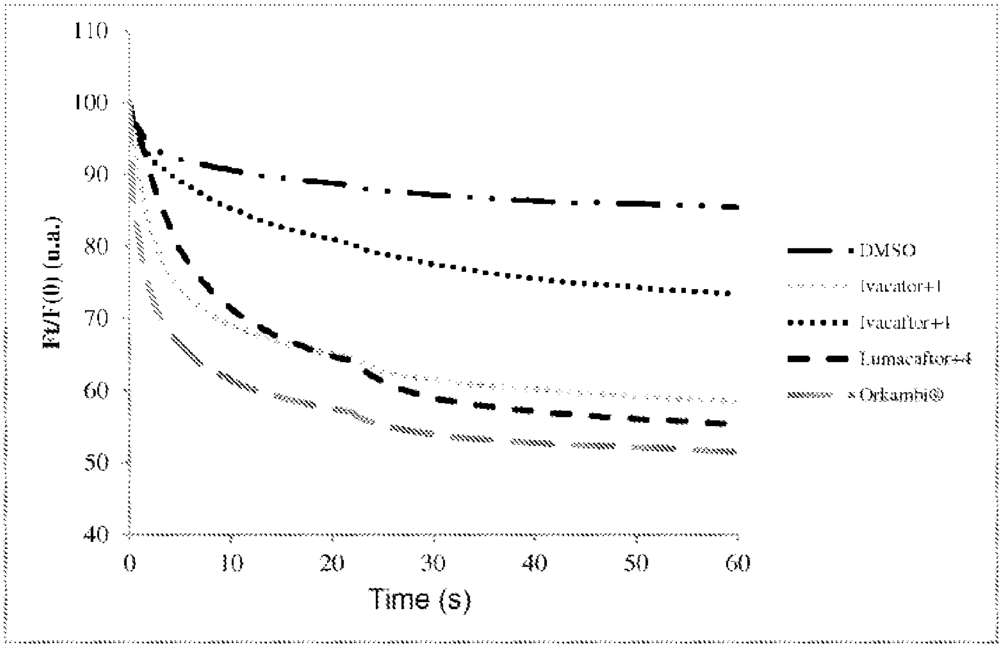

N2-ARYLMETHYL-4-HALOALKYL-PYRIDAZIN-3-ONE CFTR MODULATORS FOR THE TREATMENT OF CYSTIC FIBROSIS

CROSS-REFERENCE TO RELATED APPLICATIONS

This application is a National Stage Application of PCT/FR2020/052228 filed Nov. 30, 2020, which claims priority from French Patent Application No. 19 13404, filed on Nov. 28, 2019. The priority of said PCT and French Patent Application is claimed. Each of the prior mentioned applications is hereby incorporated by reference herein in its entirety.

FIELD OF THE INVENTION

The present invention relates to new compounds of the N2-arylmethyl-4-haloalkyl-pyridazin-3-one type of Formula I and their use in the treatment and/or prevention of diseases or conditions associated with a dysfunction of the CFTR channel activity, in particular cystic fibrosis.

BACKGROUND

Cystic fibrosis is the most common lethal hereditary genetic disease among the Caucasian population. In France, a child is born with this disease every three days. This disease is due to an autosomal recessive mutation in the CFTR (Cystic Fibrosis Transmembrane conductance Regulator) gene, which encodes the protein of the same name, a transmembrane channel which allows the exchange of ions, in particular chloride, bicarbonate and small molecules. This disease affects a multitude of organs including the lungs, pancreas, liver and intestines. Respiratory and digestive problems are the main causes of morbidity and mortality in patients.

Once diagnosed, (the test is now systematically carried out as part of post-natal care), persons affected by cystic fibrosis are followed up in specialised care centres known as CRCM (Centre de Ressources and de Competences de la Mucoviscidose). Currently, the treatment offered to them is symptomatic: it aims to reduce the manifestations of the disease and their complications. It is based essentially on taking mucolytics and bronchial fluidifiers, combined with regular physiotherapy sessions. A preventative antibiotic treatment is prescribed to limit the risk of respiratory infections. When respiratory failure is terminal, oxygen therapy becomes necessary. In order to treat extra-pulmonary manifestations, anti-inflammatory treatments, pancreatic extracts, vitamins and caloric supplementations are also prescribed. However, this symptomatic treatment is unsatisfactory due to its inconvenient nature (almost 2 h of daily care), its cost (therapeutic management, hospitalisation costs . . . ) and the sometimes evident limits to its effectiveness.

Since the discovery of the defective CFTR gene in 1989 research efforts have increased, allowing real progress in the understanding of this disease and this has opened up several avenues for therapeutic development.

The first idea to emerge was to correct the genetic defects responsible for the disease by gene therapy. This approach uses a modified viral vector to introduce and then replace the mutated gene with its normal version in lung stem cells. Clinical trials conducted to date have been disappointing because the vectors used (adenovirus, lentivirus) have appeared immunogenic and the success of targeting stem cells has been random.

The second alternative (pharmacological therapy) consists of correcting the function of the CFTR protein. The mutations responsible for dysfunctions of the CFTR chloride channel activity are divided into seven classes: absence of gene expression synthesis (IA), protein (IB), absence of protein addressing at the membrane (II), absence of function at the membrane (III), reduction of function at the membrane (IV), reduction in amount of protein at the membrane (V) and reduction in stability at the membrane (VI). The most common mutation in the population (F508del CFTR—class II) results in a misfolding of this CFTR protein onto itself, preventing it from integrating into the cell membrane. However, other versions of the mutated protein are dysfunctional even though they are present in the membrane (mutation G551 D for example—class III). It is in this context that recently the objective has been set of developing molecules which would interact with the CFTR protein to allow it to integrate into the membrane (correctors), or to improve its function when it is present but inactive (potentiators).

Thus, in 2012, the first potentiator drug, Kalydeco® (Ivacaftor) developed by the laboratories Vertex Pharmaceuticals, received a European marketing authorisation. At the time, it was only intended for patients carrying the G551D mutation (approximately 4% of diagnoses), the marketing of this drug was extended to 7 other mutations in July 2014, then to 23 additional mutations in May 2017 by the FDA. Vertex has also developed the combination of two molecules (one corrector and the other potentiator) Orkambi® (a combination of Lumacaftor, a CFTR corrector and Ivacaftor) making it possible to treat patients carrying the most common F508del mutation (detected in approximately 80% of patients on at least one allele, 2,500 patients in France).

These molecules are innovative in comparison with previously available treatments as, instead of treating the symptoms of the disease, they correct some of the cellular abnormalities associated with cystic fibrosis. However, these treatments are very expensive (220,000 euros/year for Kalydeco® and 160,000 euros/year for Orkambi®) and have serious side effects (diarrhoea, vertigo).

US patent application US 2014/274933 A1 describes phthalazinone-type compounds and their use in the treatment of pathologies involving the CFTR protein and in particular cystic fibrosis.

Patent application WO 2016/066973 A1 describes fluorinated pyridazin-3-ones and their use as PDE4 inhibitors for the treatment of the inflammatory component of bronchopulmonary conditions. However, these compounds do not target the CFTR channel.

However, there is still a need for new compounds which make it possible to restore the CFTR channel activity, specifically for the treatment of cystic fibrosis.

SUMMARY OF THE INVENTION

The inventors have now been able to develop new compounds which make it possible to restore the CFTR channel activity.

The invention thus relates to compounds of Formula I, pharmaceutically acceptable salts and solvates thereof, as well as the use of these compounds, or their solvates or compositions for the treatment and/or prevention of diseases or conditions associated with dysfunction of the CFTR channel activity.

In a first aspect, the invention relates to compounds of Formula I:

[Chem. 1]

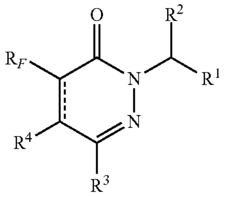

(I)

or pharmaceutically acceptable salts or solvates thereof, wherein $R^1$ is cycloalkyl, heteroaryl or aryl, optionally substituted by a group selected from alkyl, alkoxy and arylalkyl;

$R^2$ is H or alkyl;

$R^3$ is cycloalkyl, heteroaryl or aryl, optionally substituted by one or two groups selected independently from alkyl, alkoxy and haloalkoxy;

$R^4$ is H or alkyl;

$R^F$ is haloalkyl; and

⁞ is a single bond or a double bond.

According to another aspect, the invention relates to pharmaceutical compositions comprising at least one compound according to the invention or a pharmaceutically acceptable salt or solvate thereof and at least one pharmaceutically acceptable excipient As mentioned above, the invention also relates to the use of compounds according to the invention or a pharmaceutically acceptable salt or solvate thereof for restoring the CFTR channel activity. Consequently, the compounds of the invention and pharmaceutically acceptable solvates thereof are useful for the treatment and/or prevention of diseases or conditions associated with a dysfunction of the CFTR channel activity. The invention therefore also relates to compounds according to the invention for use as a drug, in particular in the treatment and/or prevention of diseases or conditions associated with a dysfunction of CFTR channel activity, in particular cystic fibrosis.

Lastly, the invention relates to pharmaceutical compositions comprising at least one compound according to the invention or a pharmaceutically acceptable salt or solvate thereof and at least one additional therapeutic agent.

Further characteristics, details and advantages are given in the following detailed description.

BRIEF DESCRIPTION OF THE DRAWINGS

FIG. 1 shows the in vitro screening of the restoration of CFTR channel activity of compounds 1 and 4 according to the invention in comparison with that of Ivacaftor, Lumacaftor and Orkambi.

FIG. 2 shows the in vitro screening of the restoration of the CFTR channel activity of compounds 1 to 6 according to the invention.

FIG. 3 shows the in vitro screening of the restoration of the CFTR channel activity of compounds 7 to 11 and 13 according to the invention.

FIG. 4 shows the in vitro evaluation of the restoration of the CFTR channel activity of the compounds according to the invention.

FIG. 5 shows the in vitro evaluation of the restoration of the CFTR channel activity of compounds 1 and 4 according to the invention in association with Ivacaftor and Lumacaftor in comparison with Orkambi.

DETAILED DESCRIPTION OF THE INVENTION

As detailed above, the invention relates to compounds of Formula I as well as the pharmaceutically acceptable solvates thereof.

Preferred compounds of Formula I and pharmaceutically acceptable salts and solvates thereof are those in which $R^1$, $R^2$, $R^3$, $R^4$ and $R_F$ are defined in the following manner:

$R^1$ is C5 to C7 cycloalkyl, C5 to C6 heteroaryl, or C6 to C10 aryl, optionally substituted by a group selected from C1 to C6 alkyl, 01 to C4 alkoxy and 01 to C4 arylalkyl; preferably $R^1$ is C5 to C6 cycloalkyl, C5 to C6 heteroaryl, or C6 aryl, optionally substituted by a group selected from C1 to C6 alkyl, C1 to C2 alkoxy and C1 to C2 arylalkyl; further preferably $R^1$ is cyclohexyl, thiophenyl, pyridinyl or phenyl, optionally substituted by a group selected from C1 to C4 alkyl, C1 to C2 alkoxy and C1 to C2 arylalkyl; more preferably $R^1$ is cyclohexyl, thiophenyl, or phenyl, optionally substituted by a group selected from methyl, methoxy and phenylethyl;

$R^2$ is H or C1 to C6 alkyl; preferably $R^2$ is H or C1 to C4 alkyl; more preferably $R^2$ is H or C1 to C2 alkyl; more preferably, $R^2$ is H or methyl; even more preferably, $R^2$ is H;

$R^3$ is C5 to C7 cycloalkyl, C4 to C6 heteroaryl, or C6 to C10 aryl, optionally substituted by one or two groups independently selected from C1 to C6 alkyl, C1 to C4 alkoxy and C1 to C4 haloalkoxy; preferably $R^3$ is C5 to C6 cycloalkyl, C4 to C6 heteroaryl, or C6 aryl, optionally substituted by one or two groups independently selected from C1 to C6 alkyl, C1 to C2 alkoxy and C1 to C2 haloalkoxy; more preferably, $R^3$ is cyclohexyl, thiophenyl, pyridinyl or phenyl optionally substituted by one or two groups independently selected from C1 to C4 alkyl, C1 to C2 alkoxy and C1 to C2 haloalkoxy; more preferably $R^3$ is cyclohexyl, pyridinyl or phenyl, optionally substituted by one or two groups independently selected from methoxy and difluoromethoxy;

$R^4$ is H or C1 to C6 alkyl; preferably $R^4$ is H or C1 to C4 alkyl; more preferably $R^4$ is H or C1 to C2 alkyl; more preferably, $R^4$ is H or methyl; even more preferably, $R^4$ is H;

$R_F$ is C1 to C6 haloalkyl; preferably, $R_F$ is C1 to C4 haloalkyl; more preferably $R_F$ is 01 to C2 haloalkyl; more preferably, $R_F$ is 01 to C2 fluoroalkyl; even more preferably, $R_F$ is trifluoromethyl.

In fact and without wishing to be bound by any theory, the inventors believe that the capacity of compounds of the invention to restore CFTR channel activity is obtained in particular due to group $R^1$ located in the benzyl position with respect to the pyridazinone or dihydropyridazinone core.

In a first embodiment, the compounds of the invention are those of Formula

[Chem. 2]

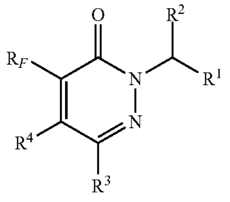

(II)

and pharmaceutically acceptable salts and solvates thereof, wherein $R^1$, $R^2$, $R^3$, $R^4$ and $R_F$ are as defined above in relation to Formula I.

Preferred compounds of Formula II are those of Formula IIa:

[Chem. 3]

(IIa)

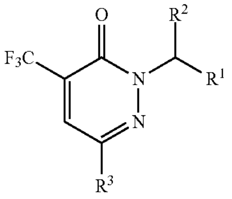

and pharmaceutically acceptable salts and solvates thereof, wherein $R^1$, $R^2$ and $R^3$ are as defined above in relation to Formula I.

Other preferred compounds of Formula II are those of Formula IIb:

[Chem. 4]

(IIb)

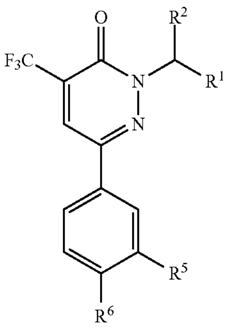

and pharmaceutically acceptable salts and solvates thereof, wherein $R^1$ and $R^2$ are as defined above in relation to Formula I, and $R^5$ and $R^6$ are selected independently from one another from alkoxy and haloalkoxy; preferably $R^5$ and $R^6$ are independently selected from C1 to C4 alkoxy and C1 to C4 haloalkoxy; more preferably $R^5$ and $R^6$ are independently selected from C1 to C2 alkoxy and C1 to C2 haloalkoxy; more preferably, $R^5$ and $R^6$ are independently selected from methoxy and difluoromethoxy.

Other preferred compounds of Formula II are those of Formula IIc:

[Chem. 5]

(IIc)

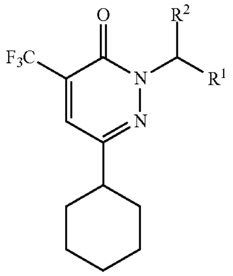

and pharmaceutically acceptable salts and solvates thereof, wherein $R^1$ and $R^2$ are as defined above in relation to Formula I.

Other preferred compounds of Formula II are those of Formula IId:

[Chem. 6]

(IId)

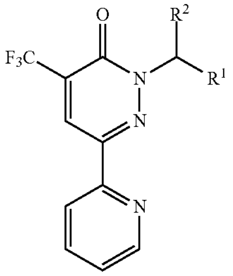

and pharmaceutically acceptable salts and solvates thereof, wherein $R^1$ and $R^2$ are as defined above in relation to Formula I.

In a second embodiment, the compounds of the invention are those of Formula III:

[Chem. 7]

(III)

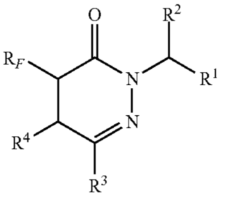

and pharmaceutically acceptable salts and solvates thereof, wherein $R^1$, $R^2$, $R^3$, $R^4$ and $R_F$ are as defined above in relation to Formula I.

Preferred compounds of Formula III are those of Formula IIIa:

[Chem. 8]

(IIIa)

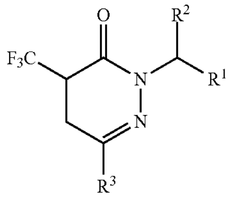

and pharmaceutically acceptable salts and solvates thereof, wherein $R^1$, $R^2$ and $R^3$ are as defined above in relation to Formula I.

Other preferred compounds of Formula III are those of Formula IIIb:

[Chem. 9]

(IIIb)

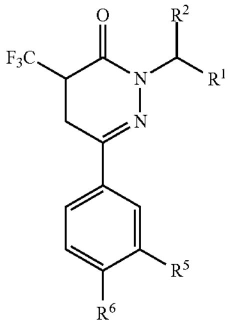

and pharmaceutically acceptable salts and solvates thereof, wherein $R^1$ and $R^2$ are as defined above in relation to Formula I, and $R^5$ and $R^6$ are selected independently from one another from alkoxy and haloalkoxy; preferably $R^5$ and $R^6$ are independently selected from C1 to C4 alkoxy and C1 to C4 haloalkoxy; more preferably $R^5$ and $R^6$ are independently selected from C1 to C2 alkoxy and C1 to C2 haloalkoxy; more preferably, $R^5$ and $R^6$ are independently selected from methoxy and difluoromethoxy.

Other preferred compounds of Formula III are those of Formula IIIc:

[Chem. 10]

(IIIc)

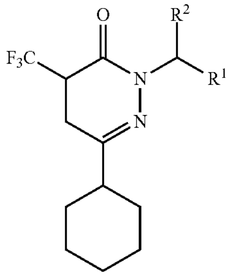

and pharmaceutically acceptable salts and solvates thereof, wherein $R^1$ and $R^2$ are as defined above in relation to Formula I.

Other preferred compounds of Formula III are those of Formula IIId:

[Chem. 11]

(IIId)

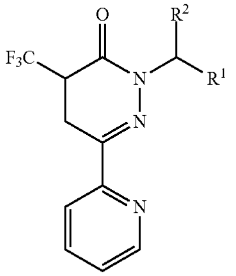

and pharmaceutically acceptable salts and solvates thereof, wherein $R^1$ and $R^2$ are as defined above in relation to Formula I.

Particularly preferred compounds of the invention are those listed in Table 1 below:

TABLE 1

| Compound | Structure | Name |
|---|---|---|
| 1 | 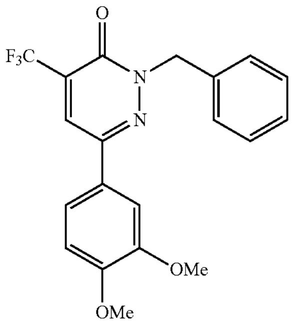 [SMILES: COc1ccc(-c2cc(C(F)(F)F)c(=O)n(Cc3ccccc3)n2)cc1OC] | 2-benzyl-6-(3,4-dimethoxyphenyl)-4-(trifluoromethyl)pyridazin-3(2H)-one |

TABLE 1-continued

| Compound | Structure | Name |
| --- | --- | --- |
| 2 | 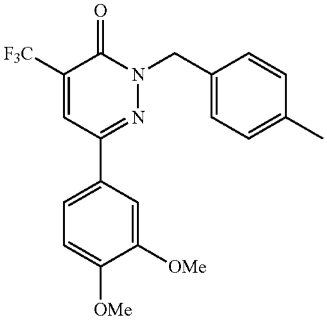 [SMILES: COc1ccc(-c2cc(C(F)(F)F)c(=O)n(Cc3ccc(C)cc3)n2)cc1OC] | 6-(3,4-dimethoxyphenyl)-2-(4-methylbenzyl)-4-(trifluoromethyl)pyridazin-3(2H)-one |
| 3 | 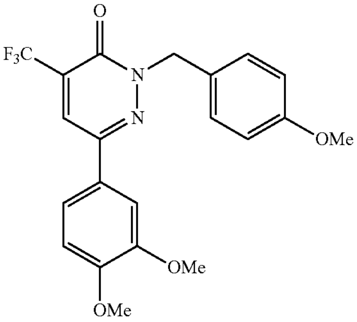 [SMILES: COc1ccc(Cn2nc(-c3ccc(OC)c(OC)c3)cc(C(F)(F)F)c2=O)cc1] | 6-(3,4-dimethoxyphenyl)-2-(4-methoxybenzyl)-4-(trifluoromethyl)pyridazin-3(2H)-one |
| 4 | 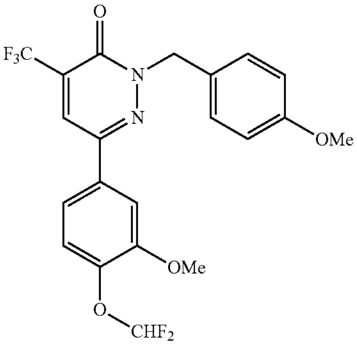 [SMILES: COc1ccc(Cn2nc(-c3ccc(OC(F)F)c(OC)c3)cc(C(F)(F)F)c2=O)cc1] | 6-(4-(difluoromethoxy)-3-methoxyphenyl)-2-(4-methoxybenzyl)-4-(trifluoromethyl)pyridazin-3(2H)-one |
| 5 | 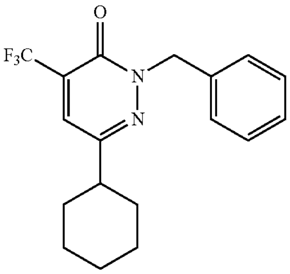 [SMILES: O=c1c(C(F)(F)F)cc(C2CCCCC2)nn1Cc1ccccc1] | 2-benzyl-6-cyclohexyl-4-(trifluoromethyl)pyridazin-3(2H)-one |
| 6 | 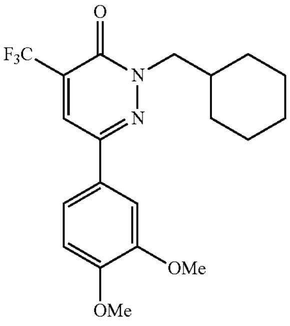 [SMILES: COc1ccc(-c2cc(C(F)(F)F)c(=O)n(CC3CCCCC3)n2)cc1OC] | 2-(cyclohexylmethyl)-6-(3,4-dimethoxyphenyl)-4-(trifluoromethyl)pyridazin-3(2H)-one |

TABLE 1-continued
| Compound | Structure | Name |
|---|---|---|
| 7 | 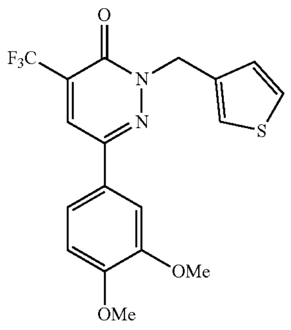 [SMILES: COc1ccc(-c2cc(C(F)(F)F)c(=O)n(Cc3ccsc3)n2)cc1OC] | 6-(3,4-dimethoxyphenyl)-2-(thiophen-3-ylmethyl)-4-(trifluoromethyl)pyridazin-3(2H)-one |
| 8 | 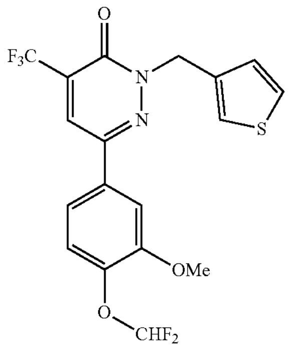 [SMILES: COc1cc(-c2cc(C(F)(F)F)c(=O)n(Cc3ccsc3)n2)ccc1OC(F)F] | 6-(4-(difluoromethoxy)-3-methoxyphenyl)-2-(thiophen-3-ylmethyl)-4-(trifluoromethyl)pyridazin-3(2H)-one |
| 9 | 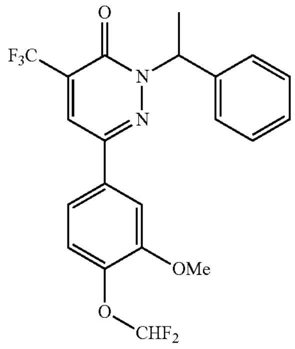 [SMILES: COc1cc(-c2cc(C(F)(F)F)c(=O)n(C(C)c3ccccc3)n2)ccc1OC(F)F] | 6-(4-(difluoromethoxy)-3-methoxyphenyl)-2-(1-phenylethyl)-4-(trifluoromethyl)pyridazin-3(2H)-one |
| 10 | 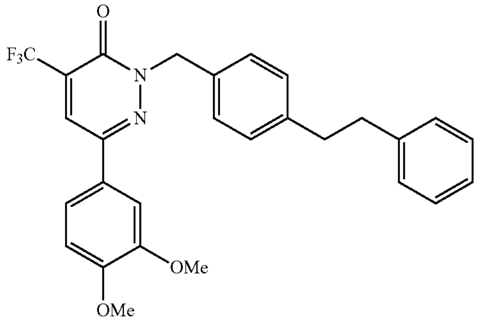 [SMILES: COc1ccc(-c2cc(C(F)(F)F)c(=O)n(Cc3ccc(CCc4ccccc4)cc3)n2)cc1OC] | 6-(3,4-dimethoxyphenyl)-2-(4-phenethylbenzyl)-4-(trifluoromethyl)pyridazin-3(2H)-one |

TABLE 1-continued
| Compound | Structure | Name |
| --- | --- | --- |
| 11 | 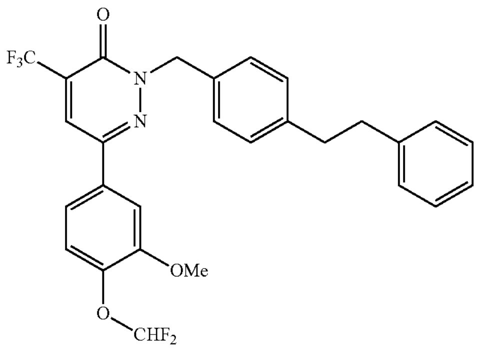 [SMILES: COc1cc(-c2cc(C(F)(F)F)c(=O)n(Cc3ccc(CCc4ccccc4)cc3)n2)ccc1OC(F)F] | 6-(4-(difluoromethoxy)-3-methoxyphenyl)-2-(4-phenethylbenzyl)-4-(trifluoromethyl)pyridazin-3(2H)-one |
| 12 | 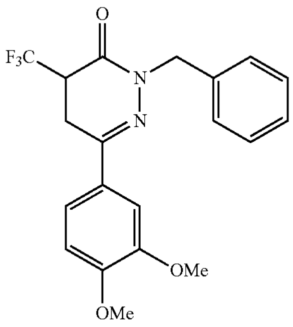 [SMILES: COc1ccc(C2=NN(Cc3ccccc3)C(=O)C(C(F)(F)F)C2)cc1OC] | 2-benzyl-6-(3,4-dimethoxyphenyl)-4-(trifluoromethyl)-4,5-dihydropyridazin-3(2H)-one |
| 13 | 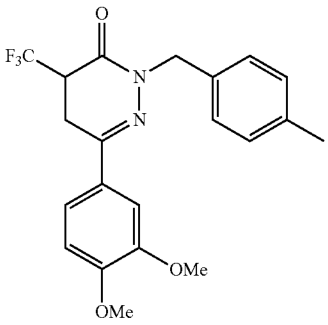 [SMILES: COc1ccc(C2=NN(Cc3ccc(C)cc3)C(=O)C(C(F)(F)F)C2)cc1OC] | 6-(3,4-dimethoxyphenyl)-2-(4-methylbenzyl)-4-(trifluoromethyl)-4,5-dihydropyridazin-3(2H)-one |
| 14 | 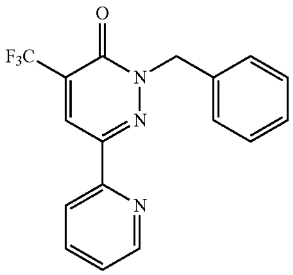 [SMILES: O=c1c(C(F)(F)F)cc(-c2ccccn2)nn1Cc1ccccc1] | 2-benzyl-6-(pyridine-2-yl)-4-(trifluoromethyl)pyridazin-3(2H)-one |

TABLE 1-continued

| Compound | Structure | Name |
|---|---|---|
| 15 | 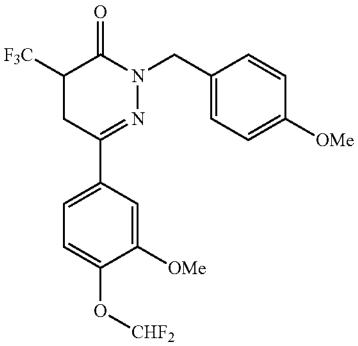 [SMILES: COc1ccc(CN2N=C(c3ccc(OC(F)F)c(OC)c3)CC(C(F)(F)F)C2=O)cc1] | 6-(4-(difluoromethoxy)-3-methoxyphenyl)-2-(4-methoxybenzyl)-4-(trifluoromethyl)-4,5-dihydropyridazin-3(2H)-one |
| 16 | 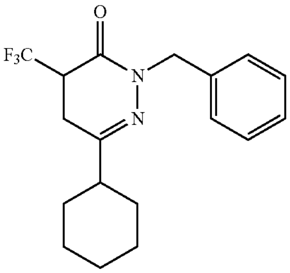 [SMILES: O=C1C(C(F)(F)F)CC(C2CCCCC2)=NN1Cc1ccccc1] | 2-benzyl-6-cyclohexyl-4-(trifluoromethyl)-4,5-dihydropyridazin-3(2H)-one |
| 17 | 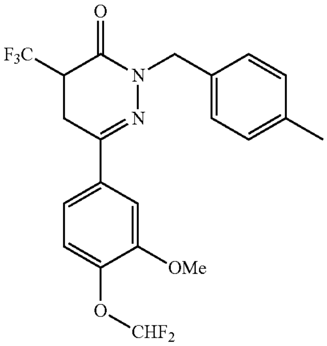 [SMILES: COc1cc(C2=NN(Cc3ccc(C)cc3)C(=O)C(C(F)(F)F)C2)ccc1OC(F)F] | 6-(4-(difluoromethoxy)-3-methoxyphenyl)-2-(4-methylbenzyl)-4-(trifluoromethyl)-4,5-dihydropyridazin-3(2H)-one |
| 18 | 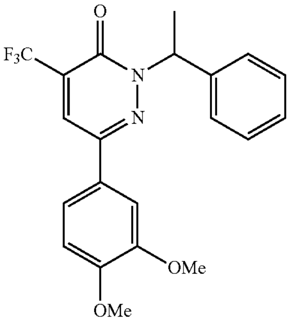 [SMILES: COc1ccc(-c2cc(C(F)(F)F)c(=O)n(C(C)c3ccccc3)n2)cc1OC] | 6-(3,4-dimethoxyphenyl)-2-(1-phenylethyl)-4-(trifluoromethyl)pyridazin-3(2H)-one |
| 19 | 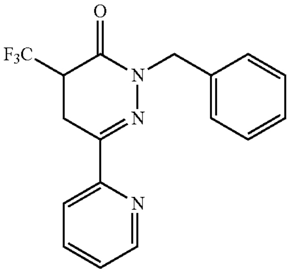 [SMILES: O=C1C(C(F)(F)F)CC(c2ccccn2)=NN1Cc1ccccc1] | 2-benzyl-6-(pyridine-2-yl)-4-(trifluoromethyl)-4,5-dihydropyridazin-3(2H)-one |

TABLE 1-continued

| Compound | Structure | Name |
|---|---|---|
| 20 | 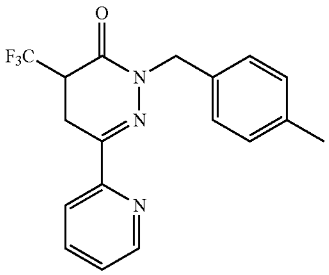 [SMILES: Cc1ccc(CN2N=C(c3ccccn3)CC(C(F)(F)F)C2=O)cc1] | 2-(4-methylbenzyl)-6-(pyridine-2-yl)-4-(trifluoromethyl)-4,5-dihydropyridazin-3(2H)-one |
| 21 | 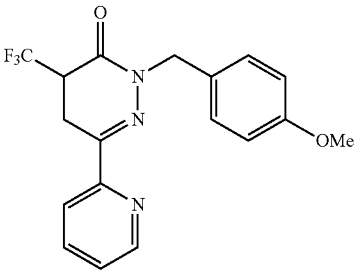 [SMILES: COc1ccc(CN2N=C(c3ccccn3)CC(C(F)(F)F)C2=O)cc1] | 2-(4-methoxybenzyl)-6-(pyridine-2-yl)-4-(trifluoromethyl)-4,5-dihydropyridazin-3(2H)-one |
| 22 | 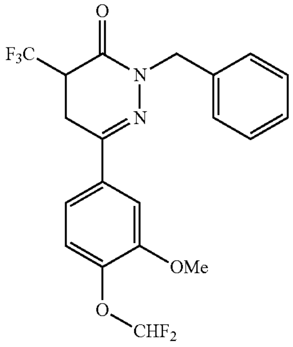 [SMILES: COc1cc(C2=NN(Cc3ccccc3)C(=O)C(C(F)(F)F)C2)ccc1OC(F)F] | 2-benzyl-6-(4-(difluoromethoxy)-3-methoxyphenyl)-4-(trifluoromethyl)-4,5-dihydropyridazin-3(2H)-one |

The compounds of Formula I can be prepared according to reactions known by the person skilled in the art. The reaction schemes described in the "Examples" section illustrate possible synthetic approaches.

In a second aspect, the invention relates to the use of compounds of the invention or pharmaceutically acceptable salts or solvates thereof for restoring CFTR channel activity.

The compounds of the invention are thus useful in the treatment and/or prevention of diseases or conditions with a dysfunction of CFTR channel activity. The invention therefore also relates to compounds according to the invention or pharmaceutically acceptable salts or solvates thereof for use as a drug, in particular for use in the treatment and/or prevention of diseases or conditions associated with a dysfunction of CFTR channel activity.

These diseases or conditions include cystic fibrosis and complications that are associated therewith.

In a preferred embodiment, the invention relates to compounds of Formula I as described above for use in the treatment of cystic fibrosis.

The present invention, according to another aspect, also relates to a method for treating diseases and conditions indicated above comprising administering to a patient an effective dose of a compound according to the invention, or pharmaceutically acceptable salts or solvates thereof. Preferably, the patient is a warm-blooded animal, more preferably a human.

According to another aspect, the invention relates to a method for restoring CFTR channel activity in a patient, preferably a warm-blooded animal, more preferably a human, in need thereof, said method comprising administering to this patient an effective dose of a compound according to the invention, or a pharmaceutically acceptable salt or solvate thereof.

According to one embodiment, the compounds of the invention, a pharmaceutically acceptable salt or solvate thereof can be administered as part of polytherapy. Thus, the scope of the present invention includes embodiments comprising the co-administration of compositions or drugs which further contain a compound of the present invention, or a pharmaceutically acceptable salt or solvate thereof as active ingredient, an additional therapeutic agent or agents and/or active ingredients. Such multiple therapeutic regimes, often referred to as polytherapy, can be used for the treatment and/or prevention of cystic fibrosis.

Thus, the methods of treatment and the pharmaceutical compositions of the present invention can use compounds of the invention or pharmaceutically acceptable salts or solvates thereof in the form of monotherapy, but these methods and compositions can also be used in the form of polytherapy in which one or more compounds of the invention or pharmaceutically acceptable salts or solvates thereof are co-administered in combination with one or more other therapeutic agents. Such additional therapeutic agents comprise, without being limited to this, Ivacaftor, Lumacaftor and/or Tezacaftor, preferably Ivacaftor. In particular, such additional therapeutic agents are selected from Ivacaftor and Lumacaftor.

The invention also relates to a pharmaceutical composition comprising at least one compound of Formula I or a pharmaceutically acceptable salt or solvate thereof and at least one pharmaceutically acceptable excipient. Said excipients are selected according to the pharmaceutical form and the desired mode of administration from the usual excipients which are known by the person skilled in the art. As indicated above, the invention also relates to pharmaceutical compositions which contain, in addition to a compound of the present invention or a pharmaceutically acceptable salt or solvate thereof as an active ingredient, an additional therapeutic agent or agents and/or active ingredients.

The pharmaceutical composition of the present invention can be selected from pharmaceutical compositions for oral, sublingual, subcutaneous, intramuscular, intravenous, topical, local, intratracheal, intranasal, transdermic or rectal administration. In these compositions, the active principle of Formula I above, or its pharmaceutically acceptable solvate, can be administered in unitary administration form, in mixture with conventional pharmaceutical excipients, to animals and humans for the treatment and/or prevention of diseases or conditions indicated above. Suitable unitary forms of administration comprise oral forms such as tablets, soft or hard capsules, powders, granules and oral solutions or suspensions, sublingual, oral, intratracheal, intraocular, intranasal forms of administration, inhalation, topical, transdermal, sub-cutaneous, intramuscular or intravenous forms of administration, rectal forms of administration and implants. For topical application the compounds according to the invention can be used in creams, gels, ointments or lotions. In a preferred embodiment, it consists of a pharmaceutical composition for oral administration. Such suitable forms of administration, which can be in solid, semi-solid or liquid form depending on the mode of administration, are generally known to the person skilled in the art, reference being made to the latest edition of "Remington's Pharmaceutical Sciences".

Definitions

The definitions and explanations given below relate to the terms and expressions used in the present application, including the description as well as the claims.

For the description of compounds of the invention, the terms and expressions used should be interpreted, unless otherwise indicated, according to the following definitions.

The term "halo" or "halogen", alone or as part of another group, refers to fluorine, chlorine, bromine, or iodine. Preferred halo groups are chlorine and fluorine, fluorine being particularly preferred.

The term "alkyl", alone or as part of another group, denotes a hydrocarbon radical of formula $C_nH_{2n+1}$ wherein n is an integer greater than or equal to 1.

The term "haloalkyl" or "halogenoalkyl", alone or as part of another group, denotes an alkyl radical as defined above, wherein one or more hydrogen atoms are replaced by a halo group as defined above. The haloalkyl radicals according to the present invention can be linear or branched, and comprise, without being limited thereto, radicals of formula $C_nF_{2n+1}$ wherein n is an integer greater than or equal to 1, preferably an integer between 1 and 10. Preferred haloalkyl radicals comprise trifluoromethyl, difluoromethyl, fluoromethyl, pentafluoroethyl, heptafluoro-n-propyl, nonafluoro-n-butyl, 1,1,1-trifluoro-n-butyl, 1,1,1-trifluoro-n-pentyl and 1,1,1-trifluoro-n-hexyl, trifluoromethyl and difluoromethyl being particularly preferred.

The term "alkoxy", alone or as part of another group, denotes an alkyl radical as defined above linked to an oxygen atom. Preferred alkoxy radicals comprise methoxy, ethoxy, propyloxy and butyloxy, methoxy being particularly preferred.

The term "haloalkoxy" or "halogenoalkoxy", alone or as part of another group, denotes a haloalkyl radical as defined above linked to an oxygen atom. Preferred haloalkoxy radicals comprise fluoromethoxy, difluoromethoxy, trifluoromethoxy, chloromethoxy, dichloromethoxy, trichloromethoxy, fluoroethoxy, difluoroethoxy, trifluoroethoxy, chloroethoxy, dichloroethoxy and trichloroethoxy, difluoromethoxy being particularly preferred.

The term "cycloalkyl", alone or as part of another group, denotes a saturated mono-, di- or tri-cyclic hydrocarbon radical having 3 to 12 carbon atoms, in particular 5 to 10 carbon atoms, more particularly 6 to 10 carbon atoms. Suitable cycloalkyl radicals include, but are not limited to cyclopropyl, cyclobutyl, cyclopentyl, cyclohexyl, cycloheptyl, cyclooctyl, norbornyl, adamantyl, in particular adamant-1-yl and adamant-2-yl, 1-decalinyl. Preferred cycloalkyl groups comprise cyclopropyl, cyclohexyl and cycloheptyl. A particularly preferred cycloalkyl group is cyclohexyl.

The term "aryl", alone or as part of another group, denotes a polyunsaturated aromatic hydrocarbon radical having a single cycle (phenyl) or multiple aromatic rings fused together (for example naphthyl) containing typically 5 to 12 atoms, preferably 6 to 10, wherein at least one of the cycles is aromatic. A particularly preferred aryl group is phenyl.

The term "heteroaryl", alone or as part of another group, denotes, without being limited thereto, aromatic cycles or cyclic systems containing one to two cycles condensed together, typically containing 5 to 12 atoms, wherein at least one of the cycles is aromatic, and wherein one or more carbon atoms in one or more of these rings are replaced by oxygen, nitrogen and/or sulphur atoms, the nitrogen and sulphur heteroatoms being optionally oxides and the nitrogen heteroatoms being optionally quaternised. Preferred heteroaryl groups which are non-limiting are pyridinyl, pyrrolyl, furanyl, thiophenyl. Particularly preferred heteroaryl groups are thiophenyl and pyridinyl.

The compounds of the invention containing a basic functional group can be in the form of pharmaceutically acceptable salts. The pharmaceutically acceptable salts of compounds of the invention containing one or more basic functional groups include, in particular, acid addition salts thereof. Suitable acid addition salts are formed from acids which form non-toxic salts. Examples of salts include acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogenophosphate/dihydrogenophosphate, pyroglutamate, saccharate, stearate, succinate, tannate, tartrate, tosylate, trifluoroacetate and xinofoate.

Pharmaceutically acceptable salts of compounds of Formula I and its sub-formulae can be prepared for example as follows:

(i) react the compound of Formula I or any of its sub-formulae with the desired acid; or (ii) convert a salt of the compound of Formula I or any of its sub-formulae into another by reaction with a suitable acid or by means of a suitable ion exchange column.

All of these reactions are generally carried out in solution. The salt can precipitate from the solution and be collected by filtration or can be recovered by evaporation of the solvent. The degree of ionisation in the salt can vary from fully ionised to almost non-ionised.

The compounds of Formula I can exist in the form of solvates, i.e. as associations or combinations with one or more solvent molecules, such as for example ethanol or water. When the solvent is water, the term "hydrate" is used.

All references to compounds of Formula I also denote the solvates thereof.

The compounds of the invention are compounds of Formula I and solvates thereof as defined above, including all polymorphs and crystalline forms thereof, prodrugs and isotopically labelled compounds or solvates thereof.

The term "patient" denotes a warm-blooded animal, preferably a human, who is waiting for or receiving a medical treatment.

The term "human" denotes subjects of both sexes and at any stage of development (i.e. neonatal, infant, juvenile, adolescent and adult). In one embodiment, this is an adolescent or adult, preferably an adult.

The terms "treat" and "treatment" should be understood with their general meaning and thus comprise the improvement and abrogation of a diseased state.

The terms "prevent" and "prevention" denote the face of avoiding or delaying the onset of a disease or condition and related symptoms, thus excluding a patient from developing a disease or condition or reducing the risk of a patient developing a disease or condition.

The term "therapeutically effective dose" or "effective dose" denotes the dose of active ingredient (compound of Formula I) which is sufficient to achieve the desired therapeutic or prophylactic result in the patient to whom it is administered.

The term "pharmaceutically acceptable" means that a compound or a component is not harmful to the patient and that in the context of a pharmaceutical composition it is compatible with the other components.

The present invention will be understood better with reference to the following examples. These examples are representative of certain embodiments of the invention and in no way limit the scope of the invention. The figures are used to illustrate the results of the experiments.

EXAMPLES

Chemical Synthesis

All temperatures are expressed in ° C. and all reactions were carried out at ambient temperature (AT), unless otherwise indicated.

The reactions were monitored by thin layer chromatography (TLC) performed on ready-to-use aluminium sheets coated with a silica gel and UV254 fluorescence indicator (Kieselgel® 60 F254 Merck, 0.2 mm thickness). The visualisation of spots is performed by UV light (254 or 366 nm). The developers used are iodine; for amines or a ninhydrine solution (0.3 g ninhydrine and 3 mL acetic acid in 100 mL butan-1-ol or 0.2 g ninhydrine in 100 mL ethanol).

The preparatory column chromatographies were carried out by the silica gel chromatographic technique. So-called normal silica column chromatographies were performed with a 60 ACC Chromagel S.D.S.® silica gel of granulometry 70 to 200 μm. The "flash" silica column chromatography is performed with a silica gel with a granulometry of 40 to 63 μm of the trademark Kieselgel 60 of Merck®.

The NMR analyses were performed on a BRUKER 199 DPX 300 spectrometer with a 7.05 T superconducting magnet (1H resonates at 300 MHz and 13C at 75 MHz. The spectra are recorded in solution either in deuterated chloroform ($CDCl_3$), with tetramethylsilane (TMS) as an internal reference, or in deuterated methanol ($CD_3OD$) or in deuterated dimethylsulfoxide (DMSO-d6). Chemical shifts are given in ppm, followed for proton spectra by the multiplicity, where s, d, t, q, dd, td and m denote respectively singlets, doublets, triplets, quadruplets, doublets of doublets, triplets of doublets and multiplets (or poorly resolved masses). The multiplicities are followed where appropriate by the value of the coupling constants noted J and expressed in Hertz (Hz).

The low mass spectra (MS) and high resolution mass spectrum (HREIMS) electronic impact (EI) at −70 eV were recorded on a WATERS MICROMASS GCT CA 170 instrument. The electrospray ionisation mass spectra (ESI), in positive mode (ESI+) or in negative mode (ESI−) were recorded on a MSQ instrument of THERMOFINNIGAN coupled to a quadripolar detector.

The solvents, reagents and starting materials were purchased from well-known chemical suppliers such as Sigma Aldrich, Acros Organics, Fluorochem, Eurisotop, VWR International, Sopachem and Polymer and, unless otherwise stated, were used without additional purifications.

The following abbreviations were used:

AcOH: acetic acid,
EA: ethyl acetate,
TLC: thin layer chromatography,
Eq. or equiv.: equivalent,
EP: petroleum ether,
EtOH: ethanol,
MeOH: methanol,
MS: mass spectrometry,
NMR: nuclear magnetic resonance,
AT: ambient temperature,
TBAB: tetrabutylammonium bromide,
TFA: trifluoroacetic acid,
THF: tetrahydrofuran.

[Scheme 1]

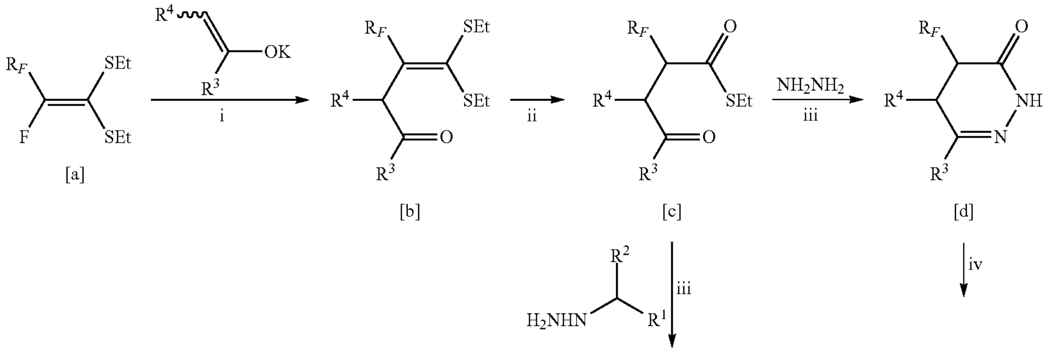

-continued

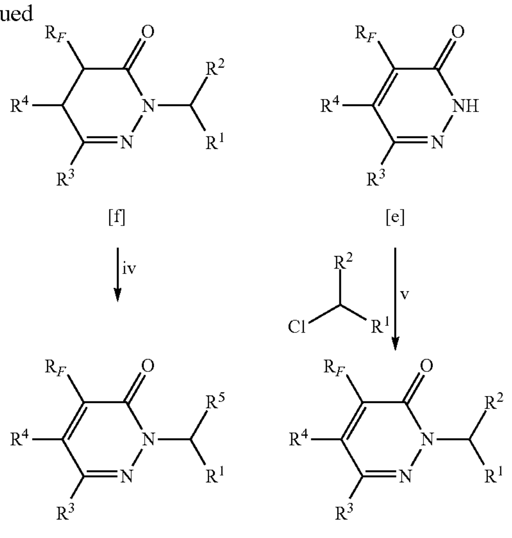

[f] [e]

II II

Reagents and conditions. (i) THF, 0-25° C., 10 h; (ii) TFA, water, reflux; (iii) AcOH, reflux or EtOH, AT; (iv) $CuCl_2$, $CH_3CN$, reflux, 4 h; (v) $K_2CO_3$, TBAB, $CH_3CN$, reflux, 4 h.

The general approach starts from a fluorinated ketene dithiocetal compound of formula [a] with $R_F$ corresponding to $CF_3$.

Compound [a] is reacted with a potassium enolate, in tetrahydrofuran (THF) as a solvent, at a temperature between 0 and 25° C. for a period of about 10 h. Thus the intermediate [b] is obtained represented in the figure and corresponding to a perfluorinated dithiocetal compound.

This intermediate of formula [b] is then subjected to an acid hydrolysis reaction in the presence of trifluoroacetic acid (TFA) and water in reflux heating. This acid hydrolysis reaction makes it possible to obtain a second thioester intermediate of formula [c].

The intermediate compound [c] can then be subjected to a condensation reaction with hydrazine ($NH_2NH_2$). The reaction is carried out in the presence of glacial acetic acid, in a reflux heater device, for a period of about 4 to 5 h. After cooling, the solvent is advantageously evaporated under vacuum. The compound [d] according to the invention is then purified by column chromatography. According to a preferred embodiment, the purification of said compound [d] is performed by chromatography on silica gel, advantageously in the presence of a mixture of petroleum ether and ethyl acetate.

The compound [d] is mixed, in an argon atmosphere in acetonitrile, with copper chloride. This mixture is refluxed for 4 h. After cooling the reaction crude is purified by column chromatography to allow compounds [e] to be obtained.

The compound [e] is mixed, under an argon atmosphere in acetonitrile, with potassium carbonate ($K_2CO_3$) and tetrabutylammonium bromide (TBAB). After 2 h the benzyl halides are added to the reaction medium. This mixture is refluxed for 4 h. After cooling the reaction crude is purified by chromatographic column to make it possible to obtain compounds according to the invention.

In a complementary manner certain compounds according to the invention can be obtained after the direct addition of functionalised benzylhydrazine to the intermediate [c]. The intermediate products [f] obtained being oxidised in the presence of copper chloride in acetonitrile. The mixture is refluxed for 4 h. After cooling, the reaction crude is purified by chromatographic column to make it possible to obtain the compounds according to the invention.

General procedure for the synthesis of the synthesis intermediates [b]

- a solution of potassium hydride and a solution of acetophenone in the presence of a solvent, preferably tetrahydrofuran (THF), is mixed preferably in an argon atmosphere at 0° C.; this constitutes mixture 1;
- a solution of perfluoroketene dithiocetal of formula [a] is added to said mixture 1, after 10 to 20 min of stirring, preferably 15 min, this constitutes mixture 2(i);
- said mixture 2 is stirred, at ambient temperature for 2 h45 to 3 h30, preferably 3 h;
- the reaction is hydrolysed while being produced within the mixture 2 with water;
- the aqueous phase of the mixture 2 is extracted, in particular with ether;
- the organic phase of the mixture 2 is dried, preferably on magnesium sulphate;
- the organic phase of the mixture 2 is filtered and evaporated, preferably under reduced pressure;
- column chromatography is carried out to obtain the compounds [b], advantageously in the form of oil.

1-(3,4-dimethoxyphenyl)-4,4-bis(ethylthio)-3-(trifluoromethyl)but-3-en-1-one [b1]

The compound [b1] is prepared according to the general procedure for the synthesis of synthesis intermediates [b] from (perfluoroprop-1-ene-1,1-diyl)bis(ethylsulfane) [a] (500 mg, 2.13 mmol, 1 eq), 1-(3,4-dimethoxyphenyl)ethanone (471 mg, 2.56 mmol, 1.2 eq) and potassium hydride (683 mg, 4.26 mmol, 2 eq) and obtained after purification by flash silica column chromatography (EP/EA: 90/10) in the form of a yellow liquid. Yield: 70% (587 mg).

NMR $^1H$ ($CDCl_3$): δ 1.22 (t, $^3J_{H,H}$=7.5 Hz, 3H, $CH_3CH_2S$), 1.34 (t, $^3J_{H,H}$=7.5 Hz, 3H, $CH_3CH_2S$), 2.81-2.91 (m, 4H, $CH_3CH_2S$), 3.93 (s, 3H, $OCH_3$), 3.97 (s, 3H, $OCH_3$), 4.40 (s, 2H, $CH_2$), 6.92 (d, $^3J_{H,H}$=8.4 Hz, 1H, $CH_{Ar}$), 7.56 (d, $^4J_{H,H}$=1.8 Hz, 1H, $CH_{Ar}$), 7.63 (dd, $^3J_{H,H}$=8.4, $^4J_{H,H}$=2.1 Hz, 1H, $CH_{Ar}$).

1-(4-difluoromethoxy)-3-methoxyphenyl)-4,4-bis(ethylthio)-3-(trifluoromethyl)but-3-en-1-one [b2]

The compound [b2] is prepared according to the general procedure for the synthesis of synthesis intermediates [b] from (perfluoroprop-1-ene-1,1-diyl)bis(ethylsulfane) [a] (187 mg, 0.8 mmol, 1 eq), 1-(4-(difluoromethoxy)-3-methoxyphenyl)ethanone (208 mg, 0.96 mmol, 1.2 eq) and potassium hydride (257 mg, 1.6 mmol, 2 eq) and obtained after purification by flash silica column chromatography (EP/EA: 98/2) in the form of colourless crystals. Yield: 85% (291 mg).

NMR $^1$H ($CDCl_3$): δ 1.26 (t, $^3J_{H,H}$=7.2 Hz, 3H, $CH_3CH_2S$), 1.34 (t, $^3J_{H,H}$=7.5 Hz, 3H, $CH_3CH_2S$), 2.81-2.91 (m, 4H, $CH_3CH_2S$), 3.94 (s, 3H, $OCH_3$), 4.41 (s, 2H, $CH_2$), 6.65 (t, $^2J_{H,F}$=74.4 Hz, 1H, $OCHF_2$), 7.25 (d, $^3J_{H,H}$=7.2 Hz, 1H, $CH_{Ar}$), 7.58 (dd, $^3J_{H,H}$=8.4, $^4J_{H,H}$=2.1 Hz, 1H, $CH_{Ar}$), 7.64 (d, $^4J_{H,H}$=2.1 Hz, 1H, $CH_{Ar}$).

1-cyclohexyl-4,4-bis(ethylthio)-3-(trifluoromethyl)but-3-en-1-one [b3]

The compound [b3] is prepared according to the general procedure for the synthesis of synthesis intermediates [b] from (perfluoroprop-1-ene-1,1-diyl)bis(ethylsulfane) [a] (700 mg, 3.0 mmol, 1 eq), 1-cyclohexylthanone (519 μL, 3.6 mmol, 1.2 eq) and potassium hydride (962 mg, 6.0 mmol, 2 eq) and obtained after purification by flash silica column chromatography (EP/EA: 99.5/0.5) in the form of a pale yellow liquid. Yield: 74% (760 mg).

NMR $^1$H ($CDCl_3$): δ 1.21 (t, $^3J_{H,H}$=7.2 Hz, 3H, $CH_3CH_2S$), 1.29 (t, $^3J_{H,H}$=7.2 Hz, 3H, $CH_3CH_2S$), 1.34-1.46 (m, 6H, 3×$CH_{2cyclohexyl}$), 1.65-1.92 (m, 4H, 2×$CH_{2cyclohexyl}$), 2.38-2.48 (m, 1H, $CH_{cyclohexyl}$), 2.83 (q, $^3J_{H,H}$=7.5 Hz, 4H, 2×$CH_3CH_2S$), 3.87 (s, 2H, $CH_2$).

4,4-bis(ethylthio)-1-(pyridine-2-yl)-3-(trifluoromethyl)but-3-en-1-one [b4]

The compound [b4] is prepared according to the general procedure for the synthesis of synthesis intermediates [b] from (perfluoroprop-1-ene-1,1-diyl)bis(ethylsulfane) [a] (469 mg, 2.0 mmol, 1 eq), of 1-(pyridine-2-yl)ethanone (291 mg, 2.4 mmol, 1.2 eq) and potassium hydride (642 mg, 4.0 mmol, 2 eq) and obtained after purification by flash silica column chromatography on (EP/EA: 95/5) in the form of a yellow liquid. Yield: 70% (561 mg).

NMR $^1$H ($CDCl_3$): δ 1.21 (t, $^3J_{H,H}$=7.2 Hz, 3H, $CH_3CH_2S$), 1.34 (t, $^3J_{H,H}$=7.5 Hz, 3H, $CH_3CH_2S$), 2.80-2.91 (m, 4H, $CH_3CH_2S$), 4.70 (s, 2H, $CH_2$), 7.48-7.53 (m, 1H, $CH_{Ar}$), 7.85 (dt, $^3J_{H,H}$=8.1, $^4J_{H,H}$=1.8 Hz, 1H, $CH_{Ar}$), 8.06 (d, $^3J_{H,H}$=7.8 Hz, 1H, $CH_{Ar}$), 8.71 (d, $^4J_{H,H}$=4.5 Hz, 1H, $CH_{Ar}$).

General Procedure for the Synthesis of Synthesis Intermediates [c]

Said compound is mixed [b] with water and trifluoroacetic acid (TFA), this constitutes mixture 3(ii);
mixture 3 is refluxed for a period of about 10 h;
after cooling, mixture 3 is neutralised with a saturated aqueous solution, preferably with $NaHCO_3$;
the aqueous phase of mixture 3 is extracted, preferably with methylene chloride;
the organic phases of mixture 3 are dried, filtered and evaporated;
column chromatography is carried out to obtain the compounds [c], advantageously in the form of oil.

S-ethyl 4-(3',4'-dimethoxyphenyl)-2-trifluoromethyl-4-oxo-butanethioate [c1]

The compound [c1] is prepared according to the general procedure for the synthesis of synthesis intermediates [c] from 1-(3,4-dimethoxyphenyl)-4,4-bis(ethylthio)-3-(trifluoromethyl)but-3-en-1-one [b1] (594 mg, 1.5 mmol, 1 eq), TFA (1.04 mL, 13.6 mmol, 9 eq) and water (0.082 mL, 4.53 mmol, 3 eq) and obtained after purification by flash silica column chromatography (EP/EA: 90/10) in the form of a yellow oil. Yield: 89% (470 mg).

NMR $^1$H ($CDCl_3$): δ 1.28 (t, $^3J_{H,H}$=7.5 Hz, 3H, $CH_3CH_2S$), 2.85-3.10 (m, 2H, $CH_3CH_2S$), 3.31 (dd, $^2J_{H,H}$=15.0, $^3J_{H,H}$=3.0 Hz, 1H, $CH_AH_BCO$), 3.85 (dd, $^2J_{H,H}$=15.0, $^3J_{H,H}$=12.0 Hz, 1H, $CH_AH_BCO$), 3.91 (s, 3H, $OCH_3$), 3.96 (s, 3H, $OCH_3$), 4.0-4.2 (m, 1H, $CHCF_3$), 6.90 (d, $^3J_{H,H}$=8.3 Hz, 1H, $CH_{Ar}$), 7.51 (d, $^4J_{H,H}$=3.0 Hz, 1H, $CH_{Ar}$), 7.61 (dd, $^3J_{H,H}$=8.3, $^4J_{H,H}$=3.0 Hz, 1H, $CH_{Ar}$).

S-ethyl 4-(4-(difluoromethoxy)-3-methoxyphenyl)-4-oxo-2-(trifluoromethyl)butanethioate [c2]

The compound [c2] is prepared according to the general procedure for the synthesis of synthesis intermediates [c] from 1-(4-difluoromethoxy)-3-methoxyphenyl)-4,4-bis(ethylthio)-3-(trifluoromethyl)but-3-en-1-one [b2] (290 mg, 0.67 mmol, 1 eq), TFA (0.467 mL, 6.06 mmol, 9 eq) and water (0.036 mL, 2.01 mmol, 3 eq) and obtained after purification by flash silica column chromatography (EP/EA: 95/5) in the form of an orange liquid. Yield: 78% (200 mg).

NMR $^1$H ($CDCl_3$): δ 1.29 (t, $^3J_{H,H}$=7.5 Hz, 3H, $CH_3CH_2S$), 2.87-3.07 (m, 2H, $CH_3CH_2S$), 3.32 (dd, $^2J_{H,H}$=18.0 Hz, $^3J_{H,H}$=3.0 Hz, 1H, $CH_AH_BCO$), 3.88 (dd, $^2J_{H,H}$=18.0 Hz, $^3J_{H,H}$=10.2 Hz, 1H, $CH_AH_BCO$), 3.94 (s, 3H, $OCH_3$), 4.02-4.15 (m, 1H, $CHCF_3$), 6.65 (t, $^2J_{H,H}$=74.3 Hz, 1H, $CHCF_2$), 7.24 (d, $^3J_{H,H}$=7.8 Hz, 1H, $CH_{Ar}$), 7.56-7.59 (m, 2H, 2×$CH_{Ar}$).

S-ethyl 4-cyclohexyl-4-oxo-2-(trifluoromethyl)butanethioate [c3]

The compound [c3] is prepared according to the general procedure for the synthesis of synthesis intermediates [c] from 1-cyclohexyl-4,4-bis(ethylthio)-3-(trifluoromethyl)but-3-en-1-one [b3] (750 mg, 2.20 mmol, 1 eq), TFA (1.527 mL, 19.8 mmol, 9 eq) and water (0.119 mL, 6.60 mmol, 3 eq) in the form of a brown liquid. Yield: 95% (618 mg).

NMR $^1$H ($CDCl_3$): δ 1.27 (t, $^3J_{H,H}$=7.5 Hz, 3H, $CH_3CH_2S$), 1.23-1.42 (m, 4H, 2×$CH_{2cyclohexyl}$), 1.66-1.94 (m, 6H, 3×$CH_{2cyclohexyl}$), 2.33-2.42 (m, 1H, $CH_{cyclohexyl}$), 2.82 (dd, $^2J_{H,H}$=18.3 Hz, $^3J_{H,H}$=3.3 Hz, 1H, $CH_AH_BCO$), 2.95 (dq, $^2J_{H,H}$=7.5 Hz, $^3J_{H,H}$=3.3 Hz, 2H, $CH_3CH_2S$), 3.32 (dd, $^2J_{H,H}$=18.3 Hz, $^3J_{H,H}$=10.2 Hz, 1H, $CH_AH_BCO$), 3.83-3.96 (m, 1H, $CHCF_3$).

S-ethyl 4-oxo-4-(pyridine-2-yl)-2-(trifluoromethyl)butanethioate [c4]

The compound [c4] is prepared according to the general procedure for the synthesis of synthesis intermediates [c] from 4,4-bis(ethylthio)-1-(pyridine-2-yl)-3-(trifluoromethyl)but-3-en-1-one [b4] (550 mg, 1.64 mmol, 1 eq), TFA (1.137 mL, 14.80 mmol, 9 eq) and water (0.088 mL, 4.92 mmol, 3 eq) and obtained after purification by flash silica column chromatography (EP/EA: 90/10) in the form of a yellow lacquer. Yield: 26% (120 mg).

$^1$H NMR ($CDCl_3$): δ 1.28 (t, $^3J_{H,H}$=7.5 Hz, 3H, $CH_3CH_2S$), 2.91-3.04 (m, 2H, $CH_3CH_2S$), 3.69 (dd, $^2J_{H,H}$=18.6 Hz, $^3J_{H,H}$=2.1 Hz, 1H, $CH_AH_BCO$), 4.02-4.20 (m, 2H, $CH_AH_BCO$, $CHCF_3$), 7.52 (ddd, $^3J_{H,H}$=7.5 Hz, $^3J_{H,H}$=4.8 Hz, $^4J_{H,H}$=1.5 Hz, 1H, $CH_{Ar}$), 7.86 (dt, $^3J_{H,H}$=7.8 Hz, $^4J_{H,H}$=1.8 Hz, 1H, $CH_{Ar}$), 8.03 (td, $^3J_{H,H}$=8.1 Hz, $^4J_{H,H}$=1.2 Hz, 1H, $CH_{Ar}$), 8.71 (d, $^3J_{H,H}$=4.5 Hz, 1H, $CH_{Ar}$).

General Procedure for the Synthesis of the Synthesis Intermediates [d]

Said compound [c] is mixed with glacial acetic acid and hydrazine monohydrate; this constitutes mixture 4(iii);

the mixture 4 is refluxed, preferably for a period of about 1 h;

after filtration, washing and drying under vacuum, the products are obtained [d] in pure form or as a mixture;

if necessary, column chromatography is performed to obtain advantageously the compounds [d].

6-(3',4'Dimethoxyphenyl)-4-trifluoromethyl-4,5-dihydropyridazin-3(2H)-one [d1]

The compound [d1] is prepared according to the general procedure for the synthesis of synthesis intermediates [d] from S-ethyl 4-(3',4'-dimethoxyphenyl)-2-trifluoromethyl-4-oxo-butanethioate [c1] (500 mg, 1.4 mmol, 1 eq) and hydrazine (35% in water) (1.616 mL, 17.8 mmol, 12.5 eq) and obtained after purification by flash silica column chromatography ($CH_2Cl_2$/MeOH: 99/1) in the form of a white solid. Yield: 76% (320 mg).

NMR $^1H$ ($CDCl_3$): δ 3.09-3.43 (m, 3H, $CH_2CHCF_3$), 3.93 (brs, 6H, 2×$OCH_3$), 6.88 (d, $^3J_{H,H}$=8.3 Hz, 1H, $CH_{Ar}$), 7.18 (d, $^3J_{H,H}$=8.3 Hz, 1H, $CH_{Ar}$), 7.40 (brs, 1H, $CH_{Ar}$), 8.91 (brs, 1H, NH).

4-(difluoromethoxy)-3-methoxyphenyl)-4-(trifluoromethyl)-4,5-dihydropyridazin-3(2H)-one [d2]

The compound [d2] is prepared according to the general procedure for the synthesis of synthesis intermediates [d] from S-ethyl 4-(4-(difluoromethoxy)-3-methoxyphenyl)-4-oxo-2-(trifluoromethyl)butanethioate [c2] (100 mg, 0.25 mmol, 1 eq) and hydrazine (35% in water) (0.282 mL, 3.13 mmol, 12.5 eq) and obtained after purification by flash silica column chromatography (PE/EA: 80/20) in the form of a beige solid. Yield: 100% (086 mg).

NMR $^1H$ ($CD_3OD$): δ 3.17 (dd, $^2J_{H,H}$=17.7 Hz, $^3J_{H,H}$=9.9 Hz, 1H, $CH_AH_BCHCF_3$), 3.37 (dd, $^2J_{H,H}$=17.4 Hz, $^3J_{H,H}$=7.5 Hz, 1H, $CH_AH_BCHCF_3$), 3.61-3.76 (m, 1H, $CHCF_3$), 6.90 (t, $^2J_{H,F}$=73.8 Hz, 1H, $OCHF_2$), 7.18 (d, $^3J_{H,H}$=9.0 Hz, 2H, 2×$CH_{Ar}$), 7.84 (d, $^3J_{H,H}$=9.0 Hz, 2H, 2×$CH_{Ar}$).

General Procedure for the Synthesis of the Synthesis Intermediates [e]

The compound [d] is mixed in an argon atmosphere in anhydrous acetonitrile with copper chloride, this constitutes mixture 5(iv);

the mixture 5 is refluxed, preferably for a period of about 4 h;

after cooling, the mixture 5 is evaporated and purified by column chromatography to obtain products [e] in the form of a solid.

6-(3',4'-Dimethoxyphenyl)-4-trifluoromethyl-pyridazin-3(2H)-one [e1]

The compound [e1] is prepared according to the general procedure for the synthesis of synthesis intermediates [e] from 6-(3',4'-dimethoxyphenyl)-4-trifluoromethyl-4,5-dihydropyridazin-3(2H)-one [d1] (300 mg, 1.0 mmol, 1 eq) and copper chloride (II) (269 mg, 2.0 mmol, 2 eq) and obtained after purification by flash silica column chromatography ($CH_2Cl_2$/MeOH: 98/2) in the form of an intense yellow solid. Yield: 85% (256 mg).

NMR $^1H$ ($CDCl_3$): δ 3.95 (s, 3H, $OCH_3$), 3.98 (s, 3H, $OCH_3$), 6.95 (d, $^3J_{H,H}$=8.3 Hz, 1H, $CH_{Ar}$), 7.29 (d, $^3J_{H,H}$=8.3 Hz, 1H, $CH_{Ar}$), 7.46 (brs, 1H, $CH_{Ar}$), 8.06 (m, 1H, $CH_{pyr}$), 11.9 (brs, 1H, NH).

6-(4-(difluoromethoxy)-3-methoxyphenyl)-4-(trifluoromethyl) pyridazin-3(2H)-one [e2]

The compound [e2] is prepared according to the general procedure for the synthesis of synthesis intermediates [e] from 6-(4-(difluoromethoxy)phenyl)-4-(trifluoromethyl)-4,5-dihydropyridazin-3(2H)-one [d2] (16 mg, 0.05 mmol, 1 eq) and copper chloride (II) (13 mg, 0.10 mmol, 2 eq) and obtained after purification by flash silica column chromatography (PE/EA: 80/20) in the form of beige crystals. Yield: 81% (13 mg).

NMR $^1H$ ($CD_3OD$): δ 3.96 (s, 3H, $OCH_3$), 6.80 (t, $^2J_{H,F}$=75.0 Hz, 1H, $OCHF_2$), 7.25 (d, $^3J_{H,H}$=8.4 Hz, 1H, $CH_{Ar}$), 7.49 (dd, $^2J_{H,H}$=8.4 Hz, $^3J_{H,H}$=1.8 Hz, 1H, $CH_{Ar}$), 7.65 (d, $^4J_{H,H}$=2.1 Hz, 1H, $CH_{Ar}$), 8.36 (d, $^5J_{H,H}$=1.2 Hz, 1H, $CH_{pyr}$).

General Procedure for the Synthesis of the Synthetic Intermediates [f]

Said compound [c] is mixed with glacial acetic acid and functionalised "benzylhydrazine"; this constitutes mixture 4(iii);

the mixture 4 is refluxed, preferably for a period of about 1 h;

the pure products [f] are obtained after filtration, washing and drying under vacuum.

2-benzyl-6-(3,4-dimethoxyphenyl)-4-(trifluoromethyl)-4,5-dihydropyridazin-3(2H)-one [f1]

The compound [f1] is prepared according to the general procedure for the synthesis of synthesis intermediates [f] from S-ethyl 4-(3',4'-dimethoxyphenyl)-2-trifluoromethyl-4-oxo-butanethioate [c1] (100 mg, 0.29 mmol, 1 eq) and dihydrochlorinated benzylhydrazine (718 mg, 3.68 mmol, 12.5 eq) and obtained by purification by flash silica column chromatography (PE/EA: 80/20) in the form of a beige solid. Yield: 47% (54 mg).

NMR $^1H$ ($CDCl_3$): δ 3.05-3.23 (m, 2H, $CH_2CHCF_3$), 3.27-3.41 (m, 1H, $CHCF_3$), 3.91 (s, 6H, 2×$OCH_3$), 5.01 (d, $^2J_{H,H}$=14.4 Hz, 1H, $NCH_AH_B$), 5.08 (d, $^2J_{H,H}$=14.4 Hz, 1H, $NCH_AH_B$), 6.86 (d, $^3J_{H,H}$=8.4 Hz, 1H, $CH_{Ar}$), 7.18 (dd, $^3J_{H,H}$=8.4 Hz, $^4J_{H,H}$=2.1 Hz, 1H, $CH_{Ar}$), 7.26-7.42 (m, 6H, 6×$CH_{Ar}$).

6-(3,4-dimethoxyphenyl)-2-(4-methylbenzyl)-4-(trifluoromethyl)-4,5-dihydropyridazin-3(2H)-one [f2]

The compound [f2] is prepared according to the general procedure for the synthesis of synthesis intermediates [f] from S-ethyl 4-(3',4'-dimethoxyphenyl)-2-trifluoromethyl-4-oxo-butanethioate [c1] (100 mg, 0.29 mmol, 1 eq) and dechlorinated 4-methylbenzylhydrazine (626 mg, 3.63 mmol, 12.5 eq) and isolated after purification by flash silica column chromatography (PE/EA: 80/20) in the form of a white solid. Yield: 32% (40 mg).

NMR $^1H$ ($CDCl_3$): δ 2.33 (s, 3H, $CH_3$), 3.05-3.25 (m, 2H, $CH_2CHCF_3$), 3.25-3.40 (m, 1H, $CHCF_3$), 3.92 (s, 3H, $OCH_3$), 3.93 (s, 3H, $OCH_3$), 4.97 (d, $^2J_{H,H}$=14.3 Hz, 1H, $NCH_AH_B$), 5.04 (d, $^2J_{H,H}$=14.3 Hz, 1H, $NCH_AH_B$), 6.87 (d, $^3J_{H,H}$=8.4 Hz, 1H, $CH_{Ar}$), 7.13 (d, $^3J_{H,H}$=7.8 Hz, 2H, 2×$CH_{Ar}$), 7.18 (dd, $^3J_{H,H}$=8.4 Hz, $^4J_{H,H}$=2.1 Hz, 1H, $CH_{Ar}$), 7.31 (d, $^3J_{H,H}$=7.8 Hz, 2H, 2×$CH_{Ar}$), 7.38 (d, $^4J_{H,H}$=2.1 Hz, 1H, $CH_{Ar}$).

6-(3,4-dimethoxyphenyl)-2-(4-methoxybenzyl)-4-(trifluoromethyl)-4,5-dihydropyridazin-3(2H)-one [f3]

The compound [f3] is prepared according to the general procedure for the synthesis of synthesis intermediates [f] from S-ethyl 4-(3',4'-dimethoxyphenyl)-2-trifluoromethyl-4-oxo-butanethioate [c1] (100 mg, 0.29 mmol, 1 eq) and 4-methoxylbenzylhydrazine (789 mg, 3.63 mmol, 12.5 eq)

and isolated after purification by flash silica column chromatography (PE/EA: 80/20) in the form of a yellow solid. Yield: 51% (62 mg).

NMR $^1$H ($CDCl_3$): δ 3.04-3.22 (m, 2H, $CH_2CHCF_3$), 3.24-3.39 (m, 1H, $CHCF_3$), 3.79 (s, 3H, $OCH_3$), 3.92 (s, 3H, $OCH_3$), 3.93 (s, 3H, $OCH_3$), 4.94 (d, $^2J_{H,H}$=14.1 Hz, 1H, $NCH_AH_B$), 5.02 (d, $^2J_{H,H}$=14.1 Hz, 1H, $NCH_AH_B$), 6.83-6.88 (m, 3H, 3×$CH_{Ar}$), 7.18 (dd, $^3J_{H,H}$=8.4 Hz, $^4J_{H,H}$=2.1 Hz, 1H, $CH_{Ar}$), 7.33-7.39 (m, 3H, 3×$CH_{Ar}$).

6-(4-(difluoromethoxy)-3-methoxyphenyl)-2-(4-methoxybenzyl)-4-(trifluoromethyl)-4,5-dihydropyridazin-3(2H)-one [f4]

The compound [f4] is prepared according to the general procedure for the synthesis of synthesis intermediates [f] from S-ethyl 4-(4-(difluoromethoxy)-3-methoxyphenyl)-4-oxo-2-(trifluoromethyl)butanethioate [c2] (100 mg, 0.26 mmol, 1 eq) and 4-methoxylbenzylhydrazine (703 mg, 3.24 mmol, 12.5 eq) and isolated after purification by flash silica column chromatography (PE/EA: 80/20) in the form of a beige solid. Yield: 62% (0.074 g).

NMR $^1$H ($CDCl_3$): δ 3.07-3.41 (m, 3H, $CH_2CHCF_3$), 3.79 (s, 3H, $OCH_3$), 3.93 (s, 3H, $OCH_3$), 4.95 (d, $^2J_{H,H}$=14.1 Hz, 1H, $NCH_AH_B$), 5.03 (d, $^2J_{H,H}$=14.1 Hz, 1H, $NCH_AH_B$), 6.59 (t, $^2J_{H,F}$=74.7 Hz, 1H, $CHF_2$), 6.86 (d, $^3J_{H,H}$=8.7 Hz, 2H, 2×$CH_{Ar}$), 7.19 (s, 2H, 2×$CH_{Ar}$), 7.35 (d, $^3J_{H,H}$=8.7 Hz, 2H, 2×$CH_{Ar}$), 7.42 (s, 1H, $CH_{Ar}$).

2-benzyl-6-cyclohexyl-4-(trifluoromethyl)-4,5-dihydropyridazin-3(2H)-one [f5]

The compound [f5] is prepared according to the general procedure for the synthesis of synthesis intermediates [f] from S-ethyl 4-cyclohexyl-4-oxo-2-(trifluoromethyl)butanethioate [c3] (150 mg, 0.50 mmol, 1 eq) and dihydrochlorinated benzylhydrazine (1257 mg, 6.25 mmol, 12.5 eq) and isolated after purification by flash silica column chromatography (PE/EA: 90/10) in the form of a beige oil. Yield: 83% (141 mg).

NMR $^1$H ($CDCl_3$): δ 1.26-1.34 (m, 5H, 5×$CH_{cyclohexyl}$), 1.68-1.82 (m, 5H, 5×$CH_{cyclohexyl}$), 2.22-2.30 (m, 1H, $CH_{cyclohexyl}$), 2.66 (s, 1H, $CH_AH_BCHCF_3$), 2.68 (s, 1H, $CH_AH_BCHCF_3$), 3.13-3.27 (m, 1H, $CHCF_3$), 4.88 (d, $^2J_{H,H}$=14.6 Hz, 1H, $NCH_AH_B$), 4.95 (d, $^2J_{H,H}$=14.6 Hz, 1H, $NCH_AH_B$), 7.24-7.35 (m, 5H, 5×$CH_{Ph}$).

2-(cyclohexylmethyl)-6-(3,4-dimethoxyphenyl)-4-(trifluoromethyl)-4,5-dihydropyridazin-3(2H)-one [f6]

The compound [f6] is prepared according to the general procedure for the synthesis of synthesis intermediates [f] from S-ethyl 4-(3',4'-dimethoxyphenyl)-2-trifluoromethyl-4-oxo-butanethioate [c1] (100 mg, 0.29 mmol, 1 eq) and hydrochlorinated cyclohexylmethylhydrazine (597 mg, 3.63 mmol, 12.5 eq) and isolated after purification by flash silica column chromatography (PE/EA: 90/10) in the form of a yellow oil. Yield: 25% (29 mg).

$^1$H NMR ($CDCl_3$): δ 0.85-0.95 (m, 2H, $CH_{2cyclohexyl}$), 1.14-1.24 (m, 2H, $CH_{2cyclohexyl}$), 1.46-1.88 (m, 7H, $CH_{cyclohexyl}$, 3×$CH_{2cyclohexyl}$), 3.07-3.23 (m, 2H, $CH_2$), 3.25-3.40 (m, 1H, CH—$CF_3$), 3.67 (dd, $^2J_{H,H}$=13.2 Hz, $^3J_{H,H}$=6.9 Hz, 1H, $NCH_2$), 3.80 (dd, $^2J_{H,H}$=13.2 Hz, $^3J_{H,H}$=7.2 Hz, 1H, $NCH_2$), 3.93 (s, 3H, $OCH_3$), 3.95 (s, 3H, $OCH_3$), 6.90 (d, $^3J_{H,H}$=8.4 Hz, 1H, $CH_{Ar}$), 7.22 (dd, $^3J_{H,H}$=8.4 Hz, $^4J_{H,H}$=2.1 Hz, 1H, $CH_{Ar}$), 7.40 (d, $^4J_{H,H}$=2.1 Hz, 1H, $CH_{Ar}$).

2-benzyl-6-(pyridine-2-yl)-4-(trifluoromethyl)-4,5-dihydropyridazin-3(2H)-one [f7]

The compound [f7] is prepared according to the general procedure for the synthesis of synthesis intermediates [f] from S-ethyl 4-oxo-4-(pyridine-2-yl)-2-(trifluoromethyl)butanethioate [c4] (73 mg, 0.25 mmol, 1 eq) and dihydrochlorinated benzylhydrazine (74 mg, 0.38 mmol, 12.5 eq) and obtained after purification by flash silica column chromatography (PE/EA: 80/20) in the form of an orange lacquer. Yield: 100% (83 mg).

$^1$H NMR ($CD_3OD$): δ 3.41 (dd, $^2J_{H,H}$=18.0 Hz, $^3J_{H,H}$=9.6 Hz, 1H, $CH_AH_BCH$—$CF_3$), 3.64 (dd, $^2J_{H,H}$=18.0 Hz, $^3J_{H,H}$=7.8 Hz, 1H, $CH_AH_BCH$—$CF_3$), 3.72-3.87 (m, 1H, $CH_2CH$—$CF_3$), 5.04 (d, $^2J_{H,H}$=14.6 Hz, 1H, $NCH_AH_B$), 5.11 (d, $^2J_{H,H}$=14.6 Hz, 1H, $NCH_AH_B$), 7.24-7.49 (m, 6H, 6×$CH_{Ar}$), 7.92 (dt, $^3J_{H,H}$=7.5 Hz, $^4J_{H,H}$=1.2 Hz, 1H, $CH_{Ar}$), 8.11 (d, $^3J_{H,H}$=7.8 Hz, 1H, $CH_{Ar}$), 8.63 (d, $^3J_{H,H}$=5.1 Hz, 1H, $CH_{Ar}$).

Example 1: 2-benzyl-6-(3,4-dimethoxyphenyl)-4-(trifluoromethyl)pyri-dazin-3(2H)-one The corresponding precursor [f1] (20 mg, 0.05 mmol, 1 eq) is dissolved, in an argon atmosphere, in anhydrous acetonitrile with copper chloride (35 mg, 0.25 mmol, 5 eq, in three additions), this constitutes mixture 5(iv). The mixture is refluxed for a period of about 4 h. After cooling and evaporation, the reaction crude is purified by flash silica column chromatography (PE/EA: 90/10) to obtain compound 1 in the form of a yellow solid. Yield: 70% (10 mg).

NMR 1H ($CDCl_3$): δ 3.94 (s, 3H, OCH3), 3.96 (s, 3H, OCH3), 5.44 (s, 2H, NCH2), 6.94 (d, 3JH,H=8.4 Hz, 1H, CHAr), 7.27 (dd, 3JH,H=8.1 Hz, 4JH,H=2.4 Hz, 1H, CHAr), 7.31-7.39 (m, 4H, 4×CHAr), 7.52 (dd, 3JH,H=7.8 Hz, 4JH,H=1.8 Hz, 1H, CHAr), 7.52 (m, 1H, CHAr), 7.93 (s, 1H, CHpyr).

Example 2: 6-(3,4-dimethoxyphenyl)-2-(4-methylbenzyl)-4-(trifluoro-methyl)pyridazin-3(2H)-one The corresponding precursor [f2] (25 mg, 0.062 mmol, 1 eq) is dissolved, in an argon atmosphere, in anhydrous acetonitrile with copper chloride (34 mg, 0.24 mmol, 4 eq, in two additions), this constitutes mixture 5(iv). The mixture is refluxed for a period of about 4 h. After cooling and evaporation, the reaction crude is purified by flash silica column chromatography (PE/EA: 85/15) to obtain compound 2 in the form of a yellow solid. Yield: 64% (20 mg).

NMR $^1$H ($CDCl_3$): δ 2.33 (s, 3H, $CH_3$), 3.94 (s, 3H, $OCH_3$), 3.96 (s, 3H, $OCH_3$), 5.39 (s, 2H, $NCH_2$), 6.93 (d, $^3J_{H,H}$=8.4 Hz, 1H, $CH_{Ar}$), 7.16 (d, $^3J_{H,H}$=8.1 Hz, 2H, 2×$CH_{Ar}$), 7.27 (dd, $^3J_{H,H}$=8.4 Hz, $^4J_{H,H}$=2.1 Hz, 1H, $CH_{Ar}$), 7.35 (d, $^4J_{H,H}$=2.1 Hz, 1H, $CH_{Ar}$), 7.42 (d, $^3J_{H,H}$=7.8 Hz, 2H, $CH_{Ar}$), 7.92 (d, 1H, $^4J_{H,H}$=1.2 Hz, $CH_{pyr}$).

Example 3: 6-(3,4-dimethoxyphenyl)-2-(4-methoxybenzyl)-4-(trifluoro-methyl)pyridazin-3(2H)-one The corresponding precursor [f3] (30 mg, 0.070 mmol, 1 eq) is dissolved, in an argon atmosphere, in anhydrous acetonitrile with copper chloride (38 mg, 0.28 mmol, 4 eq, in two additions), this constitutes mixture 5(iv). The mixture is refluxed for a period of about 4 h. After cooling and evaporation, the reaction crude is purified by flash silica column chromatography (PE/EA: 80/20) to obtain compound 3 in the form of a yellow oil. Yield: 24% (7 mg).

NMR $^1$H ($CDCl_3$): δ 3.79 (s, 3H, $OCH_3$), 3.94 (s, 3H, $OCH_3$), 3.97 (s, 3H, $OCH_3$), 5.37 (s, 1H, $NCH_2$), 6.87 (d, $^3J_{H,H}$=8.7 Hz, 2H, 2×$CH_{Ar}$), 6.94 (d, $^3J_{H,H}$=8.4 Hz, 1H, $CH_{Ar}$), 7.27 (dd, $^3J_{H,H}$=8.4 Hz, $^4J_{H,H}$=2.1 Hz, 1H, $CH_{Ar}$), 7.35 (d, $^4J_{H,H}$=2.1 Hz, 1H, $CH_{Ar}$), 7.48 (d, $^3J_{H,H}$=8.7 Hz, 2H, 2×$CH_{Ar}$), 7.91 (s, 1H, $CH_{pyr}$).

Example 4: 6-(4-(difluoromethoxy)-3-methoxyphenyl)-2-(4-methoxy-benzyl)-4-(trifluoromethyl)pyridazin-3(2H)-one The corresponding precursor [f4] (38 mg, 0.070 mmol, 1 eq) is dissolved, in an argon atmosphere, in anhydrous acetonitrile with copper chloride (19 mg, 0.14 mmol, 2 eq), this constitutes mixture 5(iv). The mixture is refluxed for a period of about 4 h. After cooling and evaporation, the reaction crude is purified by flash silica column chromatography (PE/EA: 90/10) to obtain compound 4 in the form of a yellow lacquer. Yield: 91% (30 mg).

NMR $^1$H ($CDCl_3$): δ 3.78 (s, 3H, $OCH_3$), 3.97 (s, 3H, $OCH_3$), 5.38 (s, 2H, $NCH_2$), 6.61 (t, $^2J_{H,F}$=74.4 Hz, 1H, $OCHF_2$), 6.87 (dd, $^3J_{H,H}$=8.4 Hz, $^4J_{H,H}$=1.8 Hz, 2H, 2×$CH_{Ar}$), 7.26-7.27 (m, 2H, 2×$CH_{Ar}$), 7.40 (d, $^4J_{H,H}$=1.5 Hz, 1H, $CH_{Ar}$), 7.47 (d, $^3J_{H,H}$=8.4 Hz, 2H, 2×$CH_{Ar}$), 7.91 (s, 1H, $CH_{pyr}$).

Example 5: 2-benzyl-6-cyclohexyl-4-(trifluoromethyl)pyridazin-3(2H)-one

The corresponding precursor [f5] (88 mg, 0.26 mmol, 1 eq) is dissolved, in an argon atmosphere, in anhydrous acetonitrile with copper chloride (70 mg, 0.52 mmol, 2 eq), this constitutes mixture 5(iv). The mixture is refluxed for a period of about 4 h. After cooling and evaporation, the reaction crude is purified by flash silica column chromatography (PE/EA: 95/5) to obtain compound 5 in the form of a colourless oil. Yield: 53% (50 mg).

NMR $^1$H ($CDCl_3$): δ 1.18-1.35 (m, 5H, 5×$CH_{cyclohexyl}$), 1.65-1.84 (m, 5H, 5×$CH_{cyclohexyl}$), 2.46-2.54 (m, 1H, $CH_{cyclohexyl}$), 5.23 (s, 2H, $NCH_2$), 7.18-7.29 (m, 3H, 3×$CH_{Ar}$), 7.34 (d, $^5J_{H,H}$=0.9 Hz, 1H, $CH_{pyr}$), 7.38-7.41 (m, 2H, 2×$CH_{Ar}$).

Example 6: 2-(cyclohexylmethyl)-6-(3,4-dimethoxyphenyl)-4-(trifluoro-methyl)pyridazin-3(2H)-one The corresponding precursor [f6] (15 mg, 0.038 mmol, 1 eq) is dissolved, in an argon atmosphere, in anhydrous acetonitrile with copper chloride (20 mg, 0.150 mmol, 4 eq, in two additions), this constitutes mixture 5(iv). The mixture is refluxed for a period of about 4 h. After cooling and evaporation, the reaction crude is purified by flash silica column chromatography (PE/EA: 90/10) to obtain compound 6 in the form of a yellow lacquer. Yield: 61% (90 mg).

NMR $^1$H ($CDCl_3$): δ 1.04-1.33 (m, 6H, 3×$CH_{2cyclohexyl}$), 1.70-1.74 (m, 4H, 2×$CH_{2cyclohexyl}$), 1.98-2.10 (m, 1H, $CH_{cyclohexyl}$), 3.95 (s, 3H, $OCH_3$), 3.98 (s, 3H, $OCH_3$), 4.14 (d, $^2J_{H,H}$=7.2 Hz, 2H, $NCH_2$), 6.95 (d, $^3J_{H,H}$=8.4 Hz, 1H, $CH_{Ar}$), 7.29 (dd, $^3J_{H,H}$=8.4 Hz, $^4J_{H,H}$=2.1 Hz, 1H, $CH_{Ar}$), 7.36 (d, $^4J_{H,H}$=2.1 Hz, 1H, $CH_{Ar}$), 7.94 (s, 1H, $CH_{pyr}$).

Example 7: 6-(3,4-dimethoxyphenyl)-2-(thiophen-3-ylmethyl)-4-(trifluoromethyl)pyridazin-3(2H)-one Pyridazinone N2-H [e1] (50 mg, 0.17 mmol, 1 eq) is dissolved in acetonitrile with $K_2CO_3$ (59 mg, 0.43 mmol, 2.5 eq), $Bu_4NBr$ (3 mg, 0.009 mmol, 0.05 eq), and 3-methylthiophene chloride (25 mg, 0.18 mmol, 1.1 eq), this constitutes mixture 6(v). This mixture is heated to 60° C. for a period of about 2 to 4 h. After cooling, the solvent is evaporated and the crude is taken up in water and extracted with methylene chloride. After drying the organic phase, filtration, evaporation under reduced pressure, the reaction crude is purified by flash silica column chromatography (PE/EA: 80/20) to obtain compound 7 in the form of yellow crystals. Yield: 70% (47 mg).

NMR $^1$H ($CDCl_3$): δ 3.94 (s, 3H, $OCH_3$), 3.97 (s, 3H, $OCH_3$), 5.44 (s, 2H, $NCH_2$), 6.94 (d, $^3J_{H,H}$=8.4 Hz, 1H, $CH_{Ar}$), 7.23-7.25 (m, 1H, $CH_{Ar}$), 7.29 (dd, $^3J_{H,H}$=5.1 Hz, $^4J_{H,H}$=2.7 Hz, 2H, 2×$CH_{Ar}$), 7.34 (d, $^4J_{H,H}$=2.1 Hz, 1H, $CH_{Ar}$), 7.44 (dd, $^3J_{H,H}$=2.7 Hz, $^4J_{H,H}$=1.2 Hz, 1H, $CH_{Ar}$), 7.93 (s, 1H, $CH_{pyr}$).

Example 8: 6-(4-(difluoromethoxy)-3-methoxyphenyl)-2-(thiophen-3-ylmethyl)-4-(trifluoromethyl)pyridazin-3(2H)-one Pyridazinone N2-H [e2] (50 mg, 0.15 mmol, 1 eq) is dissolved in acetonitrile with $K_2CO_3$ (52 mg, 0.38 mmol, 2.5 eq), $Bu_4NBr$ (3 mg, 0.009 mmol, 0.05 eq), and 3-methylthiophene chloride (23 mg, 0.17 mmol, 1.1 eq), this constitutes mixture 6(v). This mixture is heated to 60° C. for a period in the order of 2 to 4 h. After cooling, the solvent is evaporated and the crude is taken up in water and extracted with methylene chloride. After drying the organic phase, filtration, evaporation under reduced pressure, the reaction crude is purified by flash silica column chromatography (PE/EA: 80/20) to obtain compound 8 in the form of beige crystals. Yield: 78% (50 mg).

NMR$^1$H ($CDCl_3$): δ 4.00 (s, 3H, $OCH_3$), 5.48 (s, 2H, $NCH_2$), 6.64 (t, $^2J_{H,F}$=74.4 Hz, 1H, $OCHF_2$), 7.23 (dd, $^3J_{H,H}$=4.8 Hz, $^4J_{H,H}$=1.5 Hz, 1H, $CH_{Ar}$), 7.27 (d, $^3J_{H,H}$=2.4 Hz, 2H, 2×$CH_{Ar}$), 7.30 (dd, $^3J_{H,H}$=4.8 Hz, $^4J_{H,H}$=3.3 Hz, 1H, $CH_{Ar}$), 7.40 (d, $^3J_{H,H}$=1.8 Hz, 1H, $CH_{Ar}$), 7.44 (dd, $^3J_{H,H}$=3.0 Hz, $^4J_{H,H}$=1.2 Hz, 1H, $CH_{Ar}$), 7.92 (s, 1H, $CH_{pyr}$).

Example 9: 6-(4-(difluoromethoxy)-3-methoxyphenyl)-2-(1-phenyl-ethyl)-4-(trifluoromethyl)pyridazin-3(2H)-one Pyridazinone N2-H [e2] (100 mg, 0.30 mmol, 1 eq) is dissolved in acetonitrile with $K_2CO_3$, $Bu_4NBr$, and 1-chloro-1-phenylethane (90 μL, 0.66 mmol, 2.1 eq, in two additions), this constitutes mixture 6(v). This mixture is heated to 60° C. for a period of about 2 to 4 h. After cooling, the solvent is evaporated and the crude is taken up in water and extracted with methylene chloride. After drying the organic phase, filtration, evaporation under reduced pressure, the reaction crude is purified by trituration in diethyl ether to obtain compound 9 in the form of a beige solid. Yield: 50% (64 mg).

NMR $^1$H (DMSO-d6): δ 1.77 d, $^3J_{H,H}$=6.9 Hz, 3H, $CH_3$), 3.90 (s, 3H, $OCH_3$), 6.27 (q, $^3J_{H,H}$=6.9 Hz, 1H, $NCHCH_3$), 7.15 (t, $^2J_{H,F}$=74.4 Hz, 1H, $OCHF_2$), 7.25-7.62 (m, 6H, 6×$CH_{Ar}$), 7.57 (dd, $^3J_{H,H}$=8.4 Hz, $^4J_{H,H}$=2.1 Hz, 1H, CHAS), 7.62 (d, $^4J_{H,H}$=2.1 Hz, 1H, $CH_{Ar}$), 8.48 (s, 1H, $CH_{pyr}$).

Example 10: 6-(3,4-dimethoxyphenyl)-2-(4-phenethylbenzyl)-4-(trifluoromethyl)pyridazin-3(2H)-one Pyridazinone N2-H [e1] (50 mg, 0.17 mmol, 1 eq) is dissolved in acetonitrile with $K_2CO_3$ (59 mg, 0.43 mmol, 2.5 eq), $Bu_4NBr$ (3 mg, 0.009 mmol, 0.05 eq), and 4-(chloromethyl)-1,2-diphenylethane (42 mg, 0.18 mmol, 1.1 eq), this constitutes mixture 6(v). This mixture is heated to 60° C. for a period of about 2 to 4 h. After cooling, the solvent is evaporated and the crude is take up in water and extracted with methylene chloride. After drying the organic phase, filtration, evaporation under reduced pressure, the reaction crude is purified by flash silica column chromatography (PE/EA: 85/15) to obtain compound 10 in the form of a bright yellow lacquer. Yield: 65% (55 mg).

NMR $^1$H ($CDCl_3$) δ 2.90 (s, 4H, 2×$CH_2$), 3.94 (s, 3H, $OCH_3$), 3.96 (s, 3H, $OCH_3$), 5.41 (s, 2H, $NCH_2$), 6.94 (d, $^3J_{H,H}$=8.4 Hz, 1H, $CH_{Ar}$), 7.16-7.21 (m, 5H, 5×$CH_{Ar}$), 7.24-7.29 (m, 5H, 5×$CH_{Ar}$), 7.35 (d, $^4J_{H,H}$=2.1 Hz, 1H, $CH_{Ar}$), 7.45 (d, $^3J_{H,H}$=6.0 Hz, 2H, 2×$CH_{Ar}$), 7.93 (s, 1H, $CH_{pyr}$).

Example 11: 6-(4-(difluoromethoxy)-3-methoxyphenyl)-2-(4-phenethyl-benzyl)-4-(trifluoromethyl) pyridazin-3(2H)-one Pyridazinone N2-H [e2] (50 mg, 0.15 mmol, 1 eq) is dissolved in acetonitrile with $K_2CO_3$ (52 mg, 0.38 mmol, 2.5 eq), $Bu_4NBr$ (3 mg, 0.009 mmol, 0.05 eq), and 4-(chloromethyl)-1,2-diphenylethane (38 mg, 0.16 mmol, 1.1 eq), this constitutes mixture 6(v). This mixture is heated to 60° C. for a period of about 2 to 4 h. After cooling, the solvent is evaporated and the crude taken up in water and extracted with methylene chloride. After drying the organic phase, filtration, evaporation under reduced pressure, the reaction crude is purified by flash silica column chromatography (PE/EA: 90/10) to obtain compound 11 in the form of white crystals. Yield: 86% (69 mg).

NMR $^1H$ ($CDCl_3$) δ 2.89 (s, 4H, 2×$CH_2$), 3.96 (s, 3H, $OCH_3$), 5.41 (s, 2H, $NCH_2$), 6.61 (t, $^2J_{H,F}$=74.7 Hz, 1H, $OCHF_2$), 7.15-7.30 (m, 9H, 9×$CH_{Ar}$), 7.41-7.45 (m, 3H, 3×$CH_{Ar}$), 7.92 (d, $^5J_{H,H}$=0.9 Hz, 1H, $CH_{pyr}$).

Example 12: 2-benzyl-6-(3,4-dimethoxyphenyl)-4-(trifluoromethyl)-4,5-dihydropyridazin-3(2H)-one The precursor [c1] (100 mg, 0.29 mmol, 1 eq) is dissolved in glacial acetic acid and benzylhydrazine; this constitutes mixture 4(iii). This mixture 4 is refluxed fora period of about 1 h. After filtration, washing and drying under vacuum, the reaction crude is purified by flash silica column chromatography (PE/EA: 80/20) to obtain compound 12 in the form of a beige solid. Yield: 47% (54 mg).

NMR$^1H$ ($CDCl_3$): δ 3.05-3.23 (m, 2H, $CH_2CHCF_3$), 3.27-3.41 (m, 1H, $CHCF_3$), 3.91 (s, 6H, 2×$OCH_3$), 5.01 (d, $^2J_{H,H}$=14.4 Hz, 1H, $NCH_AH_B$), 5.08 (d, $^2J_{H,H}$=14.4 Hz, 1H, $NCH_AH_B$), 6.86 (d, $^3J_{H,H}$=8.4 Hz, 1H, $CH_{Ar}$), 7.18 (dd, $^3J_{H,H}$=8.4 Hz, $^4J_{H,H}$=2.1 Hz, 1H, $CH_{Ar}$), 7.26-7.42 (m, 6H, 6×$CH_{Ar}$).

Example 13: 6-(3,4-dimethoxyphenyl)-2-(4-methylbenzyl)-4-(trifluoro-methyl)-4,5-dihydropyridazin-3 (2H)-one The precursor [c1] (100 mg, 0.29 mmol, 1 eq) is dissolved in glacial acetic acid and 4-methylbenzylhydrazine (626 mg, 3.63 mmol, 12.5 eq), this constitutes mixture 4(iii). This mixture 4 is refluxed for a period of about 1 h. After filtration, washing and drying under vacuum, the reaction crude is purified by flash silica column chromatography (PE/EA: 80/20) to obtain compound 13 in the form of a white solid. Yield: 100% (40 mg).

NMR $^1H$ ($CDCl_3$): δ 2.33 (s, 3H, $CH_3$), 3.05-3.25 (m, 2H, $CH_2CHCF_3$), 3.25-3.40 (m, 1H, $CHCF_3$), 3.92 (s, 3H, $OCH_3$), 3.93 (s, 3H, $OCH_3$), 4.97 (d, $^2J_{H,H}$=14.3 Hz, 1H, $NCH_AH_B$), 5.04 (d, $^2J_{H,H}$=14.3 Hz, 1H, $NCH_AH_B$), 6.87 (d, $^3J_{H,H}$=8.4 Hz, 1H, $CH_{Ar}$), 7.13 (d, $^3J_{H,H}$=7.8 Hz, 2H, 2×$CH_{Ar}$), 7.18 (dd, $^3J_{H,H}$=8.4 Hz, $^4J_{H,H}$=2.1 Hz, 1H, $CH_{Ar}$), 7.31 (d, $^3J_{H,H}$=7.8 Hz, 2H, 2×$CH_{Ar}$), 7.38 (d, $^4J_{H,H}$=2.1 Hz, 1H, $CH_{Ar}$).

Example 14: 2-benzyl-6-(pyridine-2-yl)-4-(trifluoromethyl)pyridazin-3(2H)-one (14)

The corresponding precursor [f7] (30 mg, 0.90 mmol, 1 eq) is dissolved, in an argon atmosphere, in anhydrous acetonitrile with copper chloride (242 mg, 1.80 mmol, 2 eq), this constitutes mixture 5(iv). The mixture is refluxed for a period of about 4 h. After cooling and evaporation, the reaction crude is purified by flash silica column chromatography (PE/EA: 90/10) to obtain compound 14 in the form of transparent lacquer. Yield: 20% (5 mg).

NMR $^1H$ ($CDCl_3$): δ 5.46 (s, 2H, $NCH_2$), 7.32-7.39 (m, 4H, 4×$CH_{Ar}$), 7.52-7.54 (m, 2H, 2×$CH_{Ar}$), 7.83 (t, $^3J_{H,H}$=7.8 Hz, 1H, $CH_{Ar}$), 8.13 (bs, 1H, $CH_{Ar}$), 8.65 (bs, 1H, $CH_{Ar}$), 8.72 (s, 1H, $CH_{Ar}$).

Example 15: 6-(4-(difluoromethoxy)-3-methoxyphenyl)-2-(4-methoxybenzyl)-4-(trifluoromethyl)-4,5-dihydropyridazin-3(2H)-one The precursor [c2] (100 mg, 0.26 mmol, 1 eq) is dissolved in glacial acetic acid and 4-methoxybenzylhydrazine (703 mg, 3.24 mmol, 12.5 eq), this constitutes mixture 4(iii). This mixture 4 is refluxed for a period of about 1 h. After filtration, washing and drying under vacuum, the reaction crude is purified by flash silica column chromatography (PE/EA: 80/20) to obtain compound 15 in the form of a beige solid. Yield: 62% (70 mg).

NMR $^1H$ ($CDCl_3$): δ 3.07-3.41 (m, 3H, $CHCH_2CF_3$), 3.79 (s, 3H, $OCH_3$), 3.93 (s, 3H, $OCH_3$), 4.95 (d, $^2J_{H,H}$=14.1 Hz, 1H, $NCH_AH_B$), 5.03 (d, $^2J_{H,H}$=14.1 Hz, 1H, $NCH_AH_B$), 6.59 (t, $^2J_{H,F}$=74.7 Hz, 1H, $CHF_2$), 6.86 (d, $^3J_{H,H}$=8.7 Hz, 2H, 2×$CH_{Ar}$), 7.19 (s, 2H, 2×$CH_{Ar}$), 7.35 (d, $^3J_{H,H}$=8.7 Hz, 2H, 2×$CH_{Ar}$), 7.42 (s, 1H, $CH_{Ar}$).

Example 16: 2-benzyl-6-cyclohexyl-4-(trifluoromethyl)-4,5-dihydro-pyridazin-3(2H)-one The precursor [c3] (150 mg, 0.50 mmol, 1 eq) is dissolved in glacial acetic acid and benzylhydrazine, this constitutes mixture 4(iii). This mixture is refluxed for a period of about 1 h. After filtration, washing and drying under vacuum, the reaction crude is purified by flash silica column chromatography (PE/EA: 90/10) to obtain compound 16 in the form of a beige oil. Yield: 43% (50 mg).

NMR $^1H$ ($CDCl_3$): δ 1.26-1.34 (m, 5H, 5×$CH_{cyclohexyl}$), 1.68-1.82 (m, 5H, 5×$CH_{cyclohexyl}$), 2.22-2.30 (m, 1H, $CH_{cyclohexyl}$), 2.66 (s, 1H, $CH_AH_BCHCF_3$), 2.68 (s, 1H, $CH_AH_BCHCF_3$), 3.13-3.27 (m, 1H, $CHCF_3$), 4.88 (d, $^2J_{H,H}$=14.6 Hz, 1H, $NCH_AH_B$), 4.95 (d, $^2J_{H,H}$=14.6 Hz, 1H, $NCH_AH_B$), 7.24-7.35 (m, 5H, 5×$CH_{Ph}$).

Example 17: 6-(4-(difluoromethoxy)-3-methoxyphenyl)-2-(4-methylbenzyl)-4-(trifluoromethyl)-4,5-dihydropyridazin-3(2H)-one The precursor [c2] (77 mg, 0.20 mmol, 1 eq) is dissolved in glacial acetic acid and 4-methylbenzylhydrazine (340 mg, 2.50 mmol, 12.5 eq), this constitutes mixture 4(iii). This mixture is refluxed for a period of about 1 h. After filtration, washing and drying under vacuum, the reaction crude is purified by flash silica column chromatography (PE/EA: 90/10) to obtain compound 17 in the form of a beige solid. Yield: 65% (57 mg).

NMR $^1H$ ($CDCl_3$): δ 2.33(s, 3H, $CH_3$), 3.07-3.25 (m, 2H, $CH_2CHCF_3$), 3.28-3.39 (m, 1H, $CHCF_3$), 3.92 (s, 3H, $OCH_3$), 4.97 (d, $^2J_{H,H}$=14.1 Hz, 1H, $NCH_AH_B$), 5.05 (d, $^2J_{H,H}$=14.1 Hz, 1H, $NCH_AH_B$), 6.59 (t, $^2J_{H,F}$=74.7 Hz, 1H, $CHF_2$), 7.12-7.18 (m, 4H, 4×$CH_{Ar}$), 7.29 (d, $^3J_{H,H}$=7.8 Hz, 2H, 2×$CH_{Ar}$), 7.42 (s, 1H, $CH_{Ar}$).

Example 18: 6-(3,4-(dimethoxyphenyl)-2-(1-phenylethyl)-4-(trifluoromethyl)pyridazin-3(2H)-one Pyridazinone N2-H [e1] (50 mg, 0.16 mmol, 1 eq) is dissolved in acetonitrile with $K_2CO_3$ (57 mg, 0.42 mmol, 2.5 eq), $Bu_4NBr$ (3 mg, 0.007 mmol, 0.05 eq), and 1-chloro-1-phenylethane (25 μL, 0.18 mmol, 1.1 eq), this constitutes mixture 6(v). This mixture is heated to 60° C. for a period of about 2 to 4 h. After cooling, the solvent is evaporated and the crude is taken up in water and extracted with methylene chloride. After drying the organic phase, filtration, evaporation under reduced pressure, the reaction crude is purified by flash silica column chromatography (PE/EA: 90/10) to obtain compound 18 in the form of a yellow lacquer. Yield: 57% (38 mg).

NMR $^1$H ($CDCl_3$): δ 1.86 (d, $^3J_{H,H}$=7.2 Hz, 3H, $CH_3$), 3.94 (s, 3H, $OCH_3$), 3.95 (s, 3H, $OCH_3$), 6.46 (q, $^3J_{H,H}$=7.2 Hz, 1H, $NCHCH_3$), 6.94 (d, $^3J_{H,H}$=8.4 Hz, 1H, $CH_{Ar}$), 7.26-7.38 (m, 5H, 5×$CH_{Ar}$), 7.51-7.55 (m, 2H, 2×$CH_{Ar}$), 7.90 (d, $^4J_{H,H}$=0.9 Hz, 1H, $CH_{Ar}$).

Example 19: 2-benzyl-6-(pyridine-2-yl)-4-(trifluoromethyl)-4,5-dihydro pyridazin-3(2H)-one The precursor [c4] (73 mg, 0.25 mmol, 1 eq) is dissolved in glacial acetic acid and benzylhydrazine (74 mg, 0.38 mmol, 1.5 eq), this constitutes mixture 4(iii). This mixture is refluxed for a period of about 1 h. After filtration, washing and drying under vacuum, the reaction crude is purified by flash silica column chromatography (PE/EA: 80/20) to obtain compound 19 in the form of an orange lacquer. Yield: 80% (66 mg).

NMR $^1$H ($CD_3OD$): δ 3.41 (dd, $^2J_{H,H}$=18.0 Hz, $^3J_{H,H}$=9.6 Hz, 1H, $CH_AH_BCHCF_3$), 3.64 (dd, $^2J_{H,H}$=18.0 Hz, $^3J_{H,H}$=7.8 Hz, 1H, $CH_AH_BCHCF_3$), 3.72-3.87 (m, 1H, $CH_2CH$—$CF_3$), 5.04 (d, $^2J_{H,H}$=14.6 Hz, 1H, $NCH_AH_B$), 5.11 (d, $^2J_{H,H}$=14.6 Hz, 1H, $NCH_AH_B$), 7.24-7.49 (m, 6H, 6×$CH_{Ar}$), 7.92 (dt, $^3J_{H,H}$=7.5 Hz, $^4J_{H,H}$=1.2 Hz, 1H, $CH_{Ar}$), 8.11 (d, $^3J_{H,H}$=7.8 Hz, 1H, $CH_{Ar}$), 8.63 (d, $^3J_{H,H}$=5.1 Hz, 1H, $CH_{Ar}$).

Example 20: 2-(4-methylbenzyl)-6-(pyridine-2-yl)-4-(trifluoromethyl)-4,5-dihydropyridazin-3(2H)-one The precursor [c4] (44 mg, 0.15 mmol, 1 eq) is dissolved in glacial acetic acid and 4-methylbenzylhydrazine (31 mg, 0.25 mmol, 1.5 eq), this constitutes mixture 4(iii). This mixture is refluxed for a period of about 1 h. After filtration, washing and drying under vacuum, the reaction crude is purified by flash silica column chromatography (PE/EA: 90/10) to obtain compound 20 in the form of a white solid. Yield: 71% (37 mg).

NMR $^1$H ($CDCl_3$): δ 2.33 (s, 3H, $CH_3$), 3.33-3.41 (m, 2H, $CH_2CHCF_3$), 3.56-3.68 (m, 1H, CH—$CF_3$), 5.07 (d, $^2J_{H,H}$=14.3 Hz, 1H, $NCH_AH_B$), 5.05 (d, $^2J_{H,H}$=14.3 Hz, 1H, $NCH_AH_B$), 7.14 (d, $^3J_{H,H}$=7.8 Hz, 2H, 2×$CH_{Ar}$), 7.28-7.31 (m, 1H, $CH_{Ar}$), 7.31 (d, $^3J_{H,H}$=7.8 Hz, 2H, 2×$CH_{Ar}$), 7.73 (dt, $^3J_{H,H}$=7.5 Hz, $^4J_{H,H}$=1.2 Hz, 1H, $CH_{Ar}$), 8.06 (d, $^3J_{H,H}$=7.8 Hz, 1H, $CH_{Ar}$), 8.59 (d, $^3J_{H,H}$=5.1 Hz, 1H, $CH_{Ar}$).

Example 21: 2-(4-methoxybenzyl)-6-(pyridine-2-yl)-4-(trifluoromethyl)-4,5-dihydropyridazin-3(2H)-one The precursor [c4] (73 mg, 0.25 mmol, 1 eq) is dissolved in glacial acetic acid and 4-methoxybenzylhydrazine (57 mg, 0.38 mmol, 1.5 eq), this constitutes mixture 4(iii). This mixture is refluxed for a period of about 1 h. After filtration, washing and drying under vacuum, the reaction crude is purified by flash silica column chromatography (PE/EA: 90/10) to obtain compound 21 in the form of a white solid. Yield: 36% (33 mg).

NMR $^1$H ($CDCl_3$): δ 3.26-3.40 (m, 2H, $CH_2CHCF_3$), 3.55-3.68 (m, 1H, CH—$CF_3$), 3.79 (s, 3H, $OCH_3$), 4.96 (d, $^2J_{H,H}$=14.1 Hz, 1H, $NCH_AH_B$), 5.03 (d, $^2J_{H,H}$=14.1 Hz, 1H, $NCH_AH_B$), 6.86 (d, $^3J_{H,H}$=8.6 Hz, 2H, 2×$CH_{Ar}$), 7.29-7.33 (m, 1H, $CH_{Ar}$), 7.36 (d, $^3J_{H,H}$=8.6 Hz, 2H, 2×$CH_{Ar}$), 7.74 (dt, $^3J_{H,H}$=7.5 Hz, $^4J_{H,H}$=1.5 Hz, 1H, $CH_{Ar}$), 8.07 (d, $^3J_{H,H}$=8.1 Hz, 1H, $CH_{Ar}$), 8.59 (d, $^3J_{H,H}$=5.1 Hz, 1H, $CH_{Ar}$).

Example 22: 6-(4-(difluoromethoxy)-3-methoxyphenyl)-2-(4-methyl benzyl)-4-(trifluoromethyl)-4,5-dihydropyridazin-3(2H)-one The precursor [c2] (58 mg, 0.15 mmol, 1 eq) is dissolved in glacial acetic acid and benzylhydrazine (377 mg, 1.875 mmol, 12.5 eq), this constitutes the mixture 4(iii). This mixture is refluxed for a period of about 1 h. After filtration, washing and drying under vacuum, the reaction crude is purified by flash silica column chromatography (PE/EA: 80/20) to obtain compound 22 in the form of a beige solid. Yield: 70% (45 mg).

NMR $^1$H ($CDCl_3$): δ 3.09-3.26 (m, 2H, $CH_2CH$—$CF_3$), 3.31-3.45 (m, 2H, $CH_2CH$—$CF_3$), 3.91 (s, 3H, $OCH_3$), 5.02 (d, $^2J_{H,H}$=14.4 Hz, 1H, $NCH_AH_B$), 5.08 (d, $^2J_{H,H}$=14.4 Hz, 1H, $NCH_AH_B$), 6.59 (t, $^2J_{H,F}$=74.7 Hz, 1H, $CHF_2$), 7.18 (s, 2H, 2×$CH_{Ar}$), 7.38-7.41 (m, 6H, 6×$CH_{Ar}$).

Biological Evaluation

To evaluate the action of the compounds according to the invention on the restoration of CFTR activity, said compounds were tested in vitro using a suitable Premo Halid Sensor kit (Invitrogen).

The principle is based on the measurement of fluorescence (at 515-530 nm) emitted by a probe in the presence or absence of compounds of the N-benzylpyridazinone type, allowing the activity of the CFTR protein to be modulated and therefore the chloride activity of the channel to be restored.

The transport of CFTR-dependant chloride ions is thus first evaluated in osteoblasts with the use of a fluorescent probe (halide-sensitive yellow fluorescent protein (YFP)-H148Q/I152 L protein (Life Technologies, Saint Aubin, France)) (FIG. 1).

48 h after transfection of the probe into the cell, CFTR channel activity is stimulated using a solution composed of forskolin, 3-isobutyl-1-methylxanthine and apigenine (each component in a concentration of 10 μM). An iodine solution (140 mM) was then added and the fluorescence was recorded using a plate reader (400 ms/point; Ft) over a period of 60 s (baseline; F0). The decrease in the Ft/F0 ratio represents the restoration of chloride activity of the CFTR channel.

A specific CFTR channel inhibitor (CFTRinh-172 (10 μM)) is used to verify the signal from untreated osteoblasts. In the presence of this inhibitor (control) no decrease in fluorescence was observed.

For quantitative analyses, the gradients of the signals obtained are processed in non-linear regressions and correlated to the level of conductance of chloride ions.

The results obtained for compounds 1 and 4 according to the invention are shown in FIG. 1.

The measurements indicate a restoration of the CFTR channel activity (150% on average) of compounds 1 and 4 according to the invention compared with reference substances (Ivacaftor, Lumacaftor, Orkambi). FIG. 1 shows that compounds 1 and 4 allow better restoration of CFTR channel activity than those obtained with Ivacaftor and Lumacaftor, and that compound 1 allows a restoration of CFTR channel activity similar to that obtained with Orkambi.

Compounds 1 to 11 and 13 according to the invention were evaluated in a lung epithelial cell model. FIGS. 2 and 3 show the results obtained for 12 of them whose efficacy is readable after 60 seconds of recording compared with the basal condition (DMSO). These results show a restoration of CFTR channel activity from 102 to 132% on average.

FIG. 4 shows the 2 second analysis of CFTR channel activity and validates the effect of compounds 1 to 8 and 10 to 18 according to the invention compared to the basal condition. These results show a restoration of CFTR channel activity from 102% to 152% on average.

FIG. 5 shows the in vitro evaluation of the restoration of the CFTR channel activity of compounds 1 and 4 according to the invention in combination with Ivacaftor or Lumacaftor, in comparison with Orkambi.

The invention claimed is:

1. A compound of Formula I:

[Chem. 1]

(I)

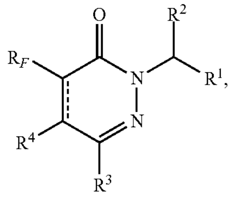

or a pharmaceutically acceptable salt or solvate thereof, wherein:

$R^1$ is cyclohexyl, thiophenyl, pyridinyl or phenyl, optionally substituted by a group selected from C1 to C4 alkyl, C1 to C2 alkoxy and C1 to C2 arylalkyl;

$R^2$ is H or alkyl;

$R^3$ is cycloalkyl, heteroaryl or aryl, optionally substituted by one or two groups selected independently from alkyl, alkoxy and haloalkoxy;

$R^4$ is H;

$R_F$ is C1 to C6 haloalkyl; and

⁝ is a single bond or a double bond.

2. The compound or salt or solvate according to claim 1, having the Formula II:

[Chem. 2]

(II)

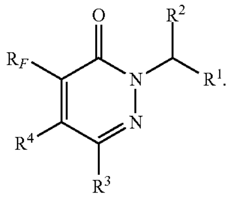

3. The compound or salt or solvate according to claim 1, having the Formula III:

[Chem. 7]

(III)

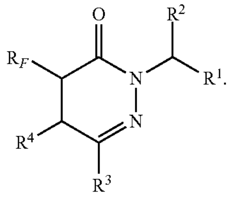

4. The compound or salt or solvate according to claim 1, selected from:

2-benzyl-6-(3,4-dimethoxyphenyl)-4-(trifluoromethyl) pyridazin-3 (2H)-one;

6-(3,4-dimethoxyphenyl)-2-(4-methylbenzyl)-4-(trifluoromethyl) pyridazin-3 (2H)-one;

6-(3,4-dimethoxyphenyl)-2-(4-methoxybenzyl)-4-(trifluoromethyl) pyridazin-3 (2H)-one;

6-(4-(difluoromethoxy)-3-methoxyphenyl)-2-(4-methoxybenzyl)-4-(trifluoromethyl) pyridazin-3 (2H)-one;

2-benzyl-6-cyclohexyl-4-(trifluoromethyl) pyridazin-3 (2H)-one;

2-(cyclohexylmethyl)-6-(3,4-dimethoxyphenyl)-4-(trifluoromethyl) pyridazin-3 (2H)-one;

6-(3,4-dimethoxyphenyl)-2-(thiophen-3-ylmethyl)-4-(trifluoromethyl) pyridazin-3 (2H)-one;

6-(4-(difluoromethoxy)-3-methoxyphenyl)-2-(thiophen-3-ylmethyl)-4-(trifluoromeethyl) pyridazin-3 (2H)-one;

6-(4-(difluoromethoxy)-3-methoxyphenyl)-2-(1-phenylethyl)-4-(trifluoromethyl) pyridazin-3 (2H)-one;

6-(3,4-dimethoxyphenyl)-2-(4-phenethylbenzyl)-4-(trifluoromethyl) pyridazin-3 (2H)-one;

6-(4-(difluoromethoxy)-3-methoxyphenyl)-2-(4-phenethylbenzyl)-4-(trifluoromethyl) pyridazin-3 (2H)-one;

2-benzyl-6-(3,4-dimethoxyphenyl)-4-(trifluoromethyl)-4,5-dihydropyridazin-3 (2H)-one;

6-(3,4-dimethoxyphenyl)-2-(4-methylbenzyl)-4-(trifluoromethyl)-4,5-dihydropyridazin-3 (2H)-one;

2-benzyl-6-(pyridine-2-yl)-4-(trifluoromethyl) pyridazin-3 (2H)-one;

6-(4-(difluoromethoxy)-3-methoxyphenyl)-2-(4-methoxybenzyl)-4-(trifluoromethyl)-4,5-dihydropyridazin-3 (2H)-one;

2-benzyl-6-cyclohexyl-4-(trifluoromethyl)-4,5-dihydropyridazin-3 (2H)-one;

6-(4-(difluoromethoxy)-3-methoxyphenyl)-2-(4-methylbenzyl)-4-(trifluoromethyl)-4,5-dihydropyridazin-3 (2H)-one;

6-(3,4-dimethoxyphenyl)-2-(1-phenylethyl)-4-(trifluoromethyl) pyridazin-3 (2H)-one;

2-benzyl-6-(pyridine-2-yl)-4-(trifluoromethyl)-4,5-dihydropyridazin-3 (2H)-one;

2-(4-methylbenzyl)-6-(pyridine-2-yl)-4-(trifluoromethyl)-4,5-dihydropyridazin-3 (2H)-one;

2-(4-methoxybenzyl)-6-(pyridine-2-yl)-4-(trifluoromethyl)-4,5-dihydropyridazin-3 (2H)-one; and 2-benzyl-6-(4-(difluoromethoxy)-3-methoxyphenyl)-4-(trifluoromethyl)-4,5-dihydropyridazin-3 (2H)-one.

5. A pharmaceutical composition, comprising at least one compound or a pharmaceutically acceptable salt or solvate thereof according to claim 1 and at least one pharmaceutically acceptable excipient.

6. A method of treatment and/or prevention of diseases or conditions associated with a dysfunction of CFTR channel activity, comprising the step of administering to a patient an effective amount of a compound according to claim 1, or a pharmaceutically acceptable salt or solvate thereof.

7. The method according to claim 6, wherein the diseases or conditions associated with a dysfunction of CFTR channel activity are cystic fibrosis and complications associated therewith.

8. A pharmaceutical composition, comprising at least one compound or a pharmaceutically acceptable salt or solvate thereof according to claim 1 and at least one additional therapeutic agent.

9. The pharmaceutical composition according to claim 8, wherein the additional therapeutic agent is selected from Ivacaftor, Lumacaftor and Tezacaftor.

* * * * *